(12) United States Patent
Kajihara et al.

(10) Patent No.: US 12,103,947 B2
(45) Date of Patent: Oct. 1, 2024

(54) METHODS FOR PRODUCING PEPTIDE THIOESTER AND PEPTIDE

(71) Applicant: GLYTECH, INC., Kyoto (JP)

(72) Inventors: Yasuhiro Kajihara, Osaka (JP); Ryo Okamoto, Osaka (JP); Yuta Maki, Osaka (JP); Yoko Amazaki, Osaka (JP); Kota Nomura, Osaka (JP); Rie Nishikawa, Osaka (JP); Takefumi Murase, Kyoto (JP)

(73) Assignee: GLYTECH, INC., Kyoto (JP)

( * ) Notice: Subject to any disclaimer, the term of this patent is extended or adjusted under 35 U.S.C. 154(b) by 658 days.

(21) Appl. No.: 17/298,125

(22) PCT Filed: Mar. 4, 2019

(86) PCT No.: PCT/JP2019/008381
§ 371 (c)(1),
(2) Date: May 28, 2021

(87) PCT Pub. No.: WO2020/110330
PCT Pub. Date: Jun. 4, 2020

(65) Prior Publication Data
US 2023/0143844 A1    May 11, 2023

(30) Foreign Application Priority Data
Nov. 30, 2018    (JP) ................. 2018-226094

(51) Int. Cl.
C07K 1/113    (2006.01)

(52) U.S. Cl.
CPC .................. C07K 1/1133 (2013.01)

(58) Field of Classification Search
CPC ...... C07K 1/026; C07K 1/107; C07K 1/1077; C07K 1/1133; A61K 38/06
See application file for complete search history.

(56) References Cited

FOREIGN PATENT DOCUMENTS

| | | | |
|---|---|---|---|
| WO | WO-9856807 A1 * | 12/1998 | ............. C07K 1/023 |
| WO | 2004005330 A1 | 1/2004 | |
| WO | 2010092943 A1 | 8/2010 | |
| WO | 2014157107 A1 | 10/2014 | |

OTHER PUBLICATIONS

Kawakami et al., "Peptide Thioester Formation by an N to S Acyl Shift Reaction at the Cysteinyl Prolyl Cysteine Position", Bull. Chem. Soc. Jpn., 2010, pp. 570-574 (Year: 2010).*

Adams et al. "Cysteine Promoted C-Terminal Hydrazinolysis of Native Peptides and Proteins" Angew. Chem. Int. Ed. vol. 52:13062-13066 (2013).
Chai et al., "N-linked glycosyl auxiliary-mediated native chemical ligation on aspartic acid: Application towards N-glycopeptide synthesis" Angewandte Chemie International Edition. vol. 55:10363-10367 (2016).
Haraguchi, Takuya et al., "Prebiotic peptide bond formation reaction using thioacids" Lecture Notes of Annual Meeting of the Chemical Society of Japan in Spring, vol. 97, p. 1C3-56 (2017).
Hou Wen et al. "A new method of N to C sequential ligation using thioacid capture ligation and native chemical ligation" Royal Society Open Science. 5:172455, 10 pages (2018).
International Search Report corresponding to International Application No. PCT/JP2019/008381 mailed May 21, 2019 (10 pages, including English translation).
Kawakami et al. "Peptide Thioester Formation by an N to S Acyl Shift Reaction at the Cysteinyl Prolyl Cysteine Position" Bull. Chem. Soc. Jpn. vol. 83(5):570-574 (2010).
Liu et al. "Acyl disulfide-mediated intramolecular acylation for orthogonal coupling between unprotected peptide segments. Mechanism and application" Tetrahedron Letters, 37(7):933-936 (1996).
Loibl et al., "A type of auxiliary for native chemical peptide ligation beyond cysteine and glycine junctions" Angewandte Chemie International Edition. vol. 54:15055-15059 (2015).
Nomura et al., "Development and research of novel glycopeptide synthesis method using amino thioacids" Lecture Notes of Annual Meeting of the Chemical Society of Japan in Spring, vol. 98, p. 1D2-07 (2018).
Ollivier et al. "Bis(2-sulfanylethyl)amino Native Peptide Ligation" Organic Letters, vol. 12(22):5238-5241 (2010).
Sumikawa et al. "Application of peptide thioacids to NCL-type sequential condensation of peptide fragments" Peptide Science, vol. 2008:175-176 (2009).
Nishikawa, Rie , et al., "A Study of Novel Glycopeptide Synthesis in Aqueous Phase using an Asparaginyl Oligosaccharide as a Ligation Site", Lecture Notes of Annual Meeting of the Chemical Society of Japan in Spring, vol. 98, p. 1 D4-31 (2018).
Chai, Hua , et al., "N-Linked Glycosyl Auxiliary-Mediated Native Chemical Ligation on Aspartic Acid: Application towards N-Glycopeptide Synthesis", Angew. Chem. Int. Ed. 55:10363-10367 (2016).

* cited by examiner

Primary Examiner — Lianko G Garyu

(74) Attorney, Agent, or Firm — Myers Bigel, P.A.

(57) ABSTRACT

An object of the present invention is to provide a novel method having high efficiency and versatility for a peptide thioester and peptide. The present invention provides a method for producing a peptide thioester, comprising the steps of: (1) providing a peptide thioester having a CGC triplet at the C-terminal; (2) causing a transfer between an SH group of the C-terminal cysteine and a carbonyl group of the glycine in the CGC triplet to obtain an R-X-CG-thioester; and (3) causing, in the R-X-CG-thioester, a transfer between the SH group of the cysteine and a carbonyl group of X, and a transfer between an amino group of the cysteine and a thiol group of the glycine to obtain a peptide thioester, and a method for producing a peptide using the peptide thioester produced by this method.

21 Claims, 15 Drawing Sheets

¹H NMR

¹H NMR

¹H NMR

FIGURE 18
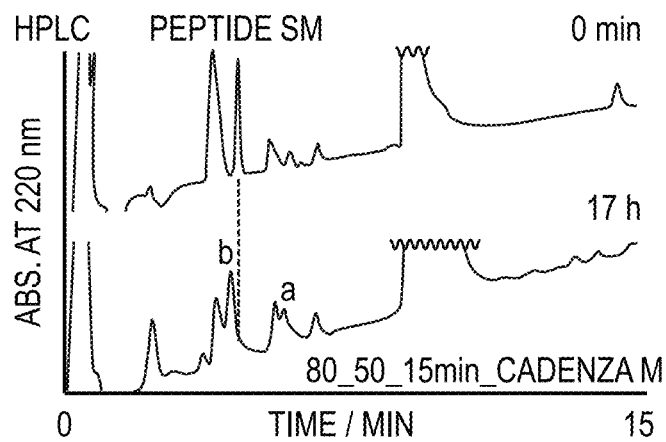
a: LIGATION PRODUCT
b: LIGATION PRODUCT (ONE PAC DEPROTECTED)
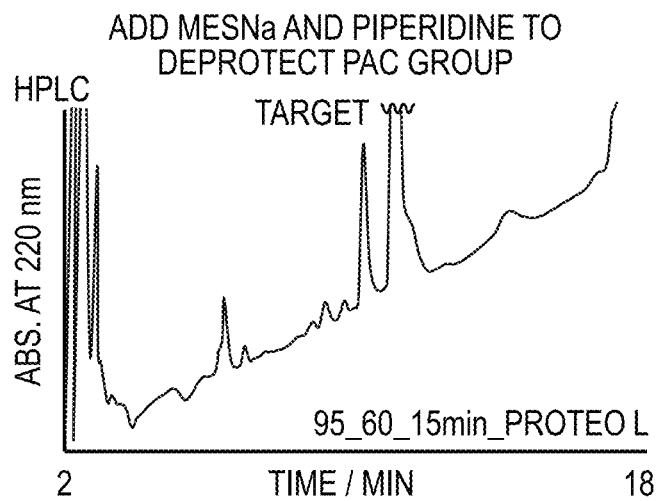
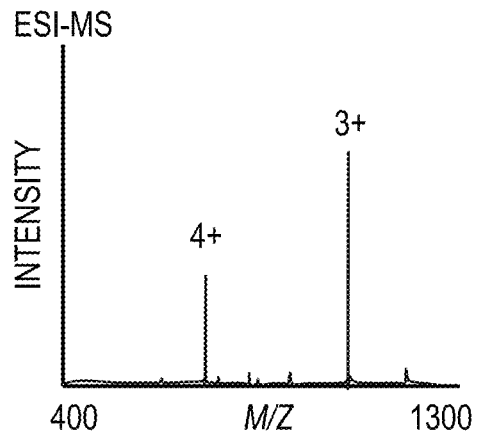

FIGURE 21
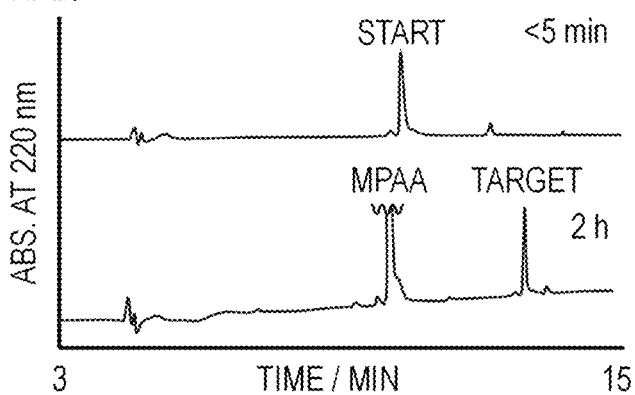
FIGURE 22
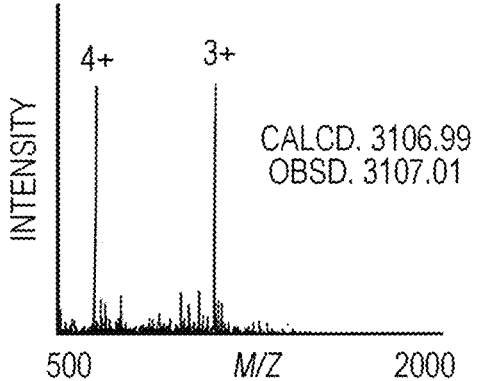
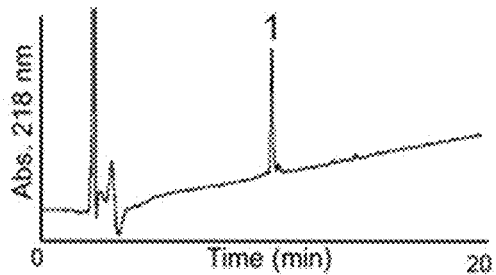
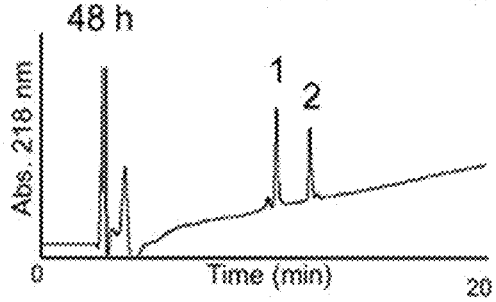
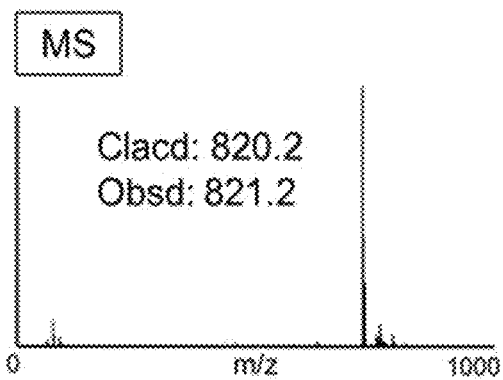

[Figure 23]
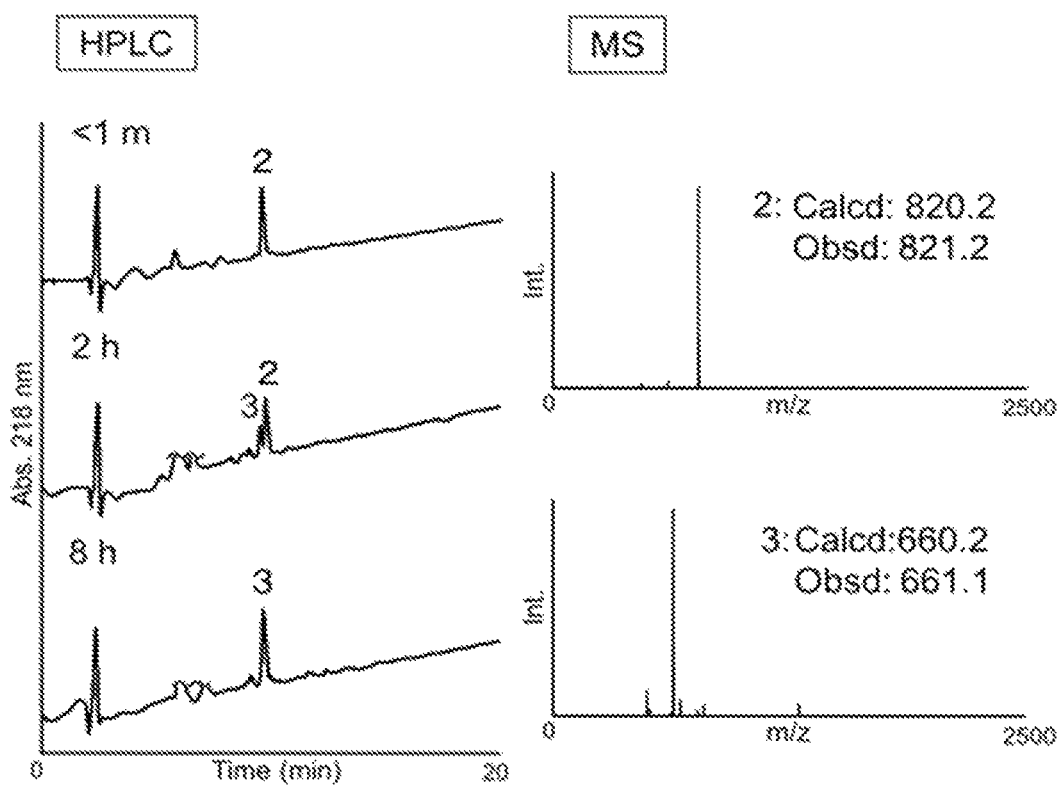

[Figure 24]
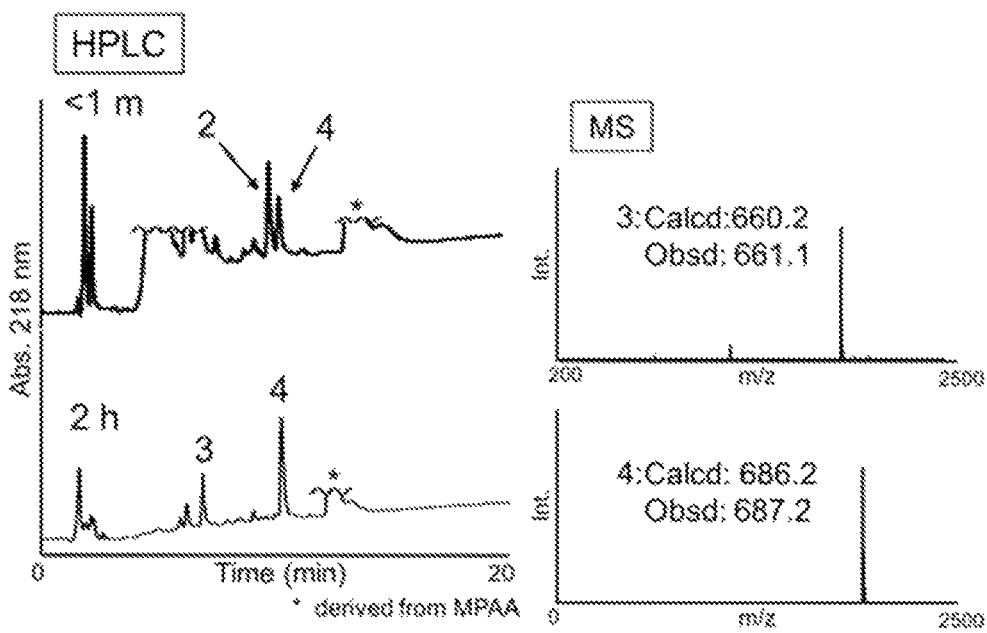
[Figure 25]
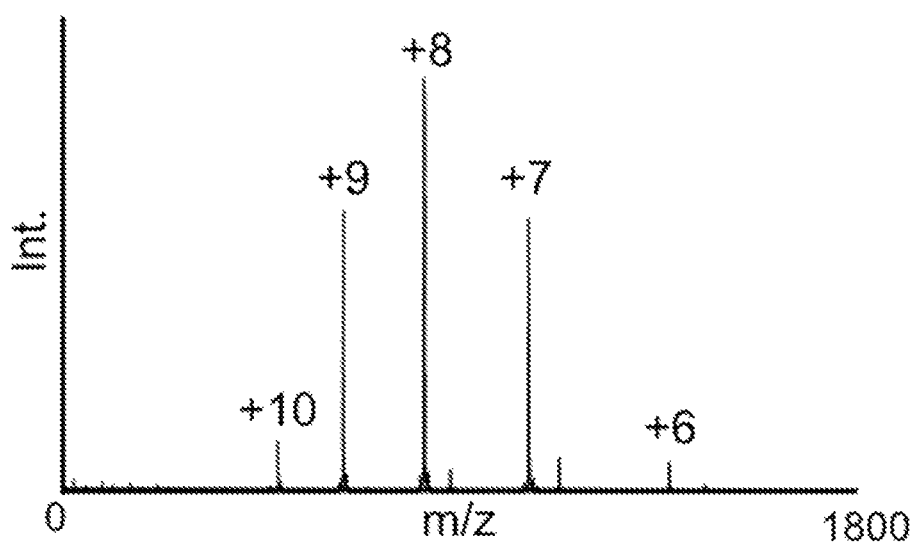

METHODS FOR PRODUCING PEPTIDE THIOESTER AND PEPTIDE

STATEMENT OF PRIORITY

This patent application is a 35 U.S.C. § 371 national phase application of PCT Application No. PCT/JP2019/008381, filed on Mar. 4, 2019, which claims priority to Japanese Application No. 2018-226094, filed Nov. 30, 2018, the entire contents of each of which are incorporated by reference herein.

TECHNICAL FIELD

The present invention relates to a novel method for a peptide thioester and peptide.

BACKGROUND ART

In chemical synthesis of a glycoprotein, particularly a glycoprotein having a large size, a method in which a protein is synthesized dividedly as some peptide fragments, and these fragments are linked to obtain a full length glycoprotein is employed (for example, Patent Literatures 1 and 2). The key to this synthesis is efficient production of a glycopeptide to be incorporated into the full length glycoprotein. Until now, as a method for producing a glycoprotein, a method in which a sugar chain-polypeptide complex is produced by using an amino acid bound to a sugar chain (glycosylated amino acid) and by applying a known peptide synthesis method such as solid phase synthesis or liquid phase synthesis (for example, Patent Literature 3) is employed. No matter whether the solid phase synthesis or the liquid phase synthesis is employed, when a free peptide and a free amino acid are condensed with a condensing agent, the amino acid reacts with a side chain functional group of the peptide. Therefore, in order to obtain a target peptide, it is necessary to repeat a condensation operation performed after protecting a portion excluding a reactive site, and a deprotection operation. The repeated reactions of the deprotection and the condensation performed in the synthesis of a glycopeptide cause a problem that a total yield of an ultimately obtained glycopeptide is lowered.

Alternatively, for synthesis of a glycoprotein, a first peptide operated to have a thioester portion at the C-terminal and a second peptide having a cysteine residue or the like are linked by the native chemical ligation (NCL) method.

Until now, a method in which a specific sequence is introduced into the C-terminal of a peptide has been reported as a synthesis method for a peptide having a thioester at the C-terminal. Kawakami et al. disclose a method in which thioesterification is performed by introducing, to the C-terminal of a peptide, a natural sequence of cysteine-proline-COOR. This method needs to activate the C-terminal with an ester, and hence cannot be applied to a peptide synthesized using an expression system because there is no method for specifically chemically modifying the C-terminal alone of an amino acid expressed in, for example, *E. coli* (Non Patent Literature 1). Ollivier et al. describe a method in which bis(2-sulfanylethyl)amine is introduced into the C-terminal of a peptide, but this method also cannot be applied to a peptide synthesized using an expression system (Non Patent Literature 2). Adams et al. describe a method in which a hydrazide or thioester is introduced into a sequence such as Gly-Cys or His-Cys present at the terminal of a chemically synthesized peptide, but this method is sequence-specific, and has a problem that reproducibility is not high (Non Patent Literature 3).

CITATION LIST

Patent Literature

Patent Literature 1
  WO2010/092943
Patent Literature 2
  WO2014/157107
Patent Literature 3
  WO2004/005330

Non Patent Literature

Non Patent Literature 1
  Kawakami et al., Bull. Chem. Soc. Jpn. Vol. 83, No. 5, 570-574 (2010)
Non Patent Literature 2
  Ollivier et al., Org. Lett., Vol. 12, No. 22, 2010
Non Patent Literature 3
  Adams et al., Angew. Chem. Int. Ed. 2013, 52, 13062-13066

SUMMARY OF INVENTION

Technical Problem

An object of the present invention is to provide a novel method having high efficiency and versatility for producing a peptide thioester and peptide.

Solution to Problem

The present invention encompasses the following characteristics:

[1] A method for producing a peptide thioester, comprising the steps of:
(1) providing a peptide having the following sequence:

[Formula 1]

$$\text{RU-XT-TGC-COOH} \tag{C1}$$

wherein R represents any amino acid sequence, X represents any amino acid, and CGC represents any amino acid triplet of cysteine-glycine-cysteine;

(2) causing a transfer between an SH group of the C-terminal cysteine and a carbonyl group of the glycine in the CGC triplet to obtain an R-X-CG-thioester; and (3) causing, in the R-X-CG-thioester, a transfer between the SH group of the cysteine and a carbonyl group of X, and ring closure condensation between an amino group of the cysteine and a carbonyl group of the thioester of the glycine to obtain a peptide thioester.

[2] The production method according to [1],
wherein the peptide is obtained by chemical synthesis, or expression by an expression system.

[3] The production method according to [1] or [2],
wherein a reaction in the step (2) is performed in the presence of at least one thiol selected from the group consisting of sodium 2-mercaptoethanesulfonate (MESNa), 2-aminoethanethiol, and bis(2-sulfanylethyl)amine.

[4] The production method according to any one of [1] to [3],
wherein a reaction in the step (3) is performed in the presence of at least one thiol selected from sodium 2-mercaptoethanesulfonate (MESNa), mercaptophenylacetic acid (MPAA), 2-mercaptopropionic acid, thiophenol, benzyl mercaptan, and ¾-mercapto-benzylsulfonate.

[5] The production method according to any one of [1] to [4], further comprising (2-1) of purifying the R-X-CG-thioester after the reaction of the step (2) and before the step (3).

[6] The production method according to any one of [1] to [5], wherein the peptide is a glycosylated peptide.

[7] A method for producing a peptide, comprising a step of condensing:

(A) a peptide thioester produced by the production method according to any one of [1] to [6]; and (B) an amino thioacid or peptide thioacid, to obtain a peptide, wherein at least some of side chains of amino acids constituting (A) and (B) is unprotected.

[8] The method for producing a peptide according to [7], wherein all of the side chains of the amino acids constituting (A) and (B) are unprotected.

[9] The method for producing a peptide according to [7] or [8], wherein the production method is a method for producing a glycosylated peptide.

[10] The method for producing a peptide according to [9], wherein the peptide thioester is a glycosylated peptide thioester.

[11] The method for producing a peptide according to [9], wherein the amino thioacid or peptide thioacid is a glycosylated amino thioacid or glycosylated peptide thioacid.

[12] The method for producing a peptide according to [11], wherein the glycosylated amino thioacid is a thioacid of a glycosylated amino acid selected from the group consisting of Asn, Ser, Thr, Hyl, and Hyp.

[13] The method for producing a peptide according to [11], wherein a glycosylated amino acid in the glycosylated peptide thioacid is a glycosylated amino acid selected from the group consisting of Asn, Ser, Thr, Hyl and Hyp.

[14] The method for producing a peptide according to [11] or [13], wherein the glycosylated peptide thioacid is obtained by reacting a glycosylated amino thioacid with a peptide having, at an N-terminal, a cysteine having, in a side chain thereof, a modifying group capable of forming a disulfide bond to a thioic acid group (—SH) in the glycosylated amino thioacid to introduce the thioic acid group into a C-terminal of the peptide resulting from the reaction.

[15] The method for producing a peptide according to [14], wherein the modifying group is a modifying group selected from the group consisting of:

[Formula 2]

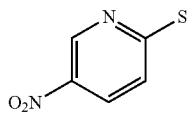

-continued

[Formula 3]

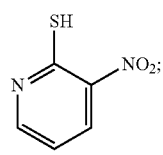

and

[Formula 4]

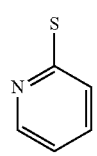

[16] A method for producing a peptide, comprising a step of condensing:

(a) a peptide thioester produced by the production method according to any one of [1] to [6]; and (b) an amino acid or peptide having an auxiliary group having the following structure introduced into an N-terminal thereof:

X—C(SH)—Y    [Formula 5]

wherein X represents any substituent separated by an acid treatment, a base treatment, a light irradiation treatment, or a reduction treatment; and Y represents a ketone or an aldehyde, to obtain a peptide, wherein at least some of side chains of amino acids constituting (a) and (b) is unprotected.

[17] The method for producing a peptide according to [16], wherein X represents aryl.

[18] The method for producing a peptide according to [16] or [17], wherein all of the side chains of the amino acids constituting (a) and (b) are unprotected.

[19] The method for producing a peptide according to any one of [16] to [18], wherein the production method is a method for producing a glycosylated peptide.

[20] The method for producing a peptide according to [19], wherein the peptide thioester is a glycosylated peptide thioester.

[21] The method for producing a peptide according to [19], wherein the "amino acid or peptide having an auxiliary group introduced into an N-terminal thereof" is a glycosylated amino acid or glycosylated peptide having the auxiliary group introduced into an N-terminal thereof.

[22] The method for producing a peptide according to [21], wherein the "glycosylated amino acid having the auxiliary group introduced into an N-terminal thereof" is selected from the group consisting of glycosylated Asn, glycosylated Ser, glycosylated Thr, and glycosylate Hyl having the auxiliary group introduced into an N-terminal thereof.

[23] The method for producing a peptide according to [22], wherein the "glycosylated amino acid having the auxiliary group introduced into an N-terminal thereof" is a glycosylated amino acid having the following structure:

[Formula 6]

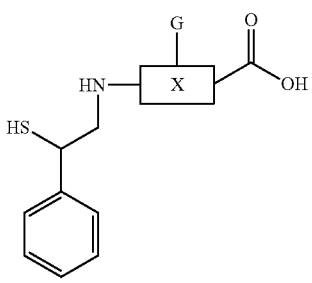

wherein X represents any amino acid, and G represents any sugar chain.

[24] The method for producing a peptide according to [23],
wherein the amino acid X is selected from the group consisting of Asn, Ser, Thr, and Hyl.

[25] The method for producing a peptide according to [22],
wherein the "glycosylated amino acid having the auxiliary group introduced into an N-terminal thereof" is a glycosylated dipeptide having the following structure:

[Formula 7]

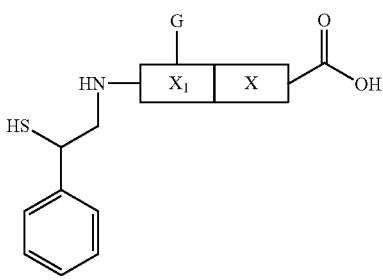

wherein $X_1$ represents Asn, Ser, Thr, or Hyl, X represents any amino acid, and G represents any sugar chain.

[26] A method for producing a peptide, comprising a step of condensing:
(AA) a peptide thioester; and
(BB) an amino thioacid or peptide thioacid, to obtain a peptide,
wherein at least some of side chains of amino acids constituting (AA) and (BB) is unprotected.

[27] The method for producing a peptide according to [26],
wherein all of the side chains of the amino acids constituting (AA) and (BB) are unprotected.

[28] The method for producing a peptide according to [26] or [27],
wherein the production method is a method for producing a glycosylated peptide.

[29] The method for producing a peptide according to [28],
wherein the peptide thioester is a glycosylated peptide thioester.

[30] The method for producing a peptide according to [28],
wherein the amino thioacid or peptide thioacid is a glycosylated amino thioacid or glycosylated peptide thioacid.

[31] The method for producing a peptide according to [30],
wherein the glycosylated amino thioacid is a thioacid of a glycosylated amino acid selected from the group consisting of Asn, Ser, Thr, Hyl, and Hyp.

[32] The method for producing a peptide according to [30],
wherein a glycosylated amino acid in the glycosylated peptide thioacid is a glycosylated amino acid selected from the group consisting of Asn, Ser, Thr, Hyl, and Hyp.

[33] The method for producing a peptide according to [30] or [32],
wherein the glycosylated peptide thioacid is obtained by reacting a glycosylated amino thioacid with a peptide having, at an N-terminal, a cysteine having, in a side chain thereof, a modifying group capable of forming a disulfide bond to a thioic acid group (—SH) in the glycosylated amino thioacid to introduce the thioic acid group to a C-terminal of the peptide resulting from the reaction.

[34] The method for producing a peptide according to [33],
wherein the modifying group is a modifying group selected from the group consisting of:

[Formula 8]

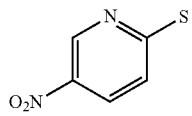

[Formula 9]

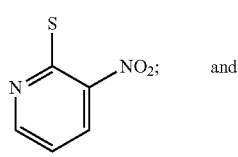
and

[Formula 10]

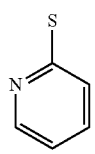

[35] A method for producing a peptide, comprising a step of condensing:
(aa) a peptide thioester; and
(bb) an amino acid or peptide having an auxiliary group having the following structure introduced into an N-terminal thereof:

X—C(SH)—Y [Formula 11]

wherein X represents any substituent separated by an acid treatment, a base treatment, a light irradiation treatment, or a reduction treatment; and Y represents a ketone or an aldehyde, to obtain a peptide,
wherein at least some of side chains of amino acids constituting (aa) and (bb) is unprotected.

[36] The method for producing a peptide according to [35],
wherein X represents aryl.

[37] The method for producing a peptide according to [35] or [36],
wherein all of the side chains of the amino acids constituting (aa) and (bb) are unprotected.

[38] The method for producing a peptide according to any one of [35] to [37],
wherein the production method is a method for producing a glycosylated peptide.

[39] The method for producing a peptide according to [38],
wherein the peptide thioester is a glycosylated peptide thioester.

[40] The method for producing a peptide according to [38],
wherein the "amino acid or peptide having an auxiliary group introduced into an N-terminal thereof" is a glycosylated amino acid or glycosylated peptide having the auxiliary group introduced into an N-terminal thereof.

[41] The method for producing a peptide according to [40],
wherein the "glycosylated amino acid having the auxiliary group introduced into an N-terminal thereof" is selected from the group consisting of glycosylated Asn, glycosylated Ser, glycosylated Thr, and glycosylated Hyl having the auxiliary group introduced into an N-terminal thereof.

[42] The method for producing a peptide according to [40],
wherein the "glycosylated amino acid having the auxiliary group introduced into an N-terminal thereof" is a glycosylated amino acid having the following structure:

[Formula 12]

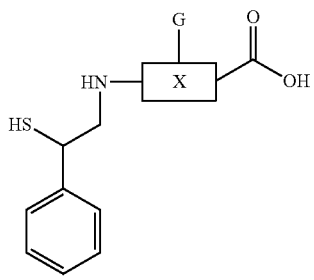

wherein X represents any amino acid, and G represents any sugar chain.

[43] The method for producing a peptide according to [42],
wherein the amino acid X is selected from the group consisting of Asn, Ser, Thr, and Hyl.

[44] The method for producing a peptide according to [40],
wherein the "glycosylated amino acid having the auxiliary group introduced into an N-terminal thereof" is a glycosylated dipeptide having the following structure:

[Formula 13]

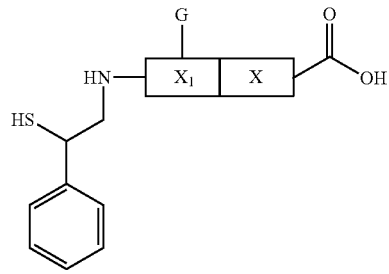

wherein $X_1$ represents Asn, Ser, Thr, or Hyl, X represents any amino acid, and G represents any sugar chain.

[45] A glycosylated amino acid having the following structure:

[Formula 14]

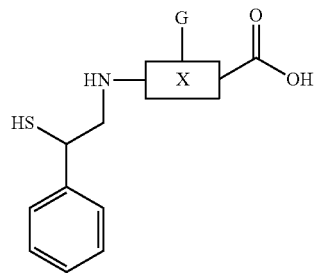

wherein X represents any amino acid, and G represents any sugar chain.

[46] The glycosylated amino acid according to [45],
wherein the amino acid X is selected from the group consisting of Asn, Ser, Thr, and Hyl.

[47] A glycosylated dipeptide having the following structure:

[Formula 15]

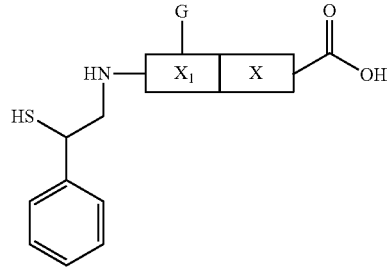

wherein $X_1$ represents Asn, Ser, Thr, or Hyl, X represents any amino acid, and G represents any sugar chain.

Those skilled in the art would understand that an invention resulting from any combination of one or a plurality of characteristics of the present invention described above also falls in the scope of the present invention.

Advantageous Effects of Invention

According to a production method of the present invention, a novel method having high efficiency and versatility for producing a peptide thioester and peptide are provided.

BRIEF DESCRIPTION OF DRAWINGS

FIG. 18 illustrates an HPLC profile and an ESI-MS spectrum of a reaction product of ligation between a sugar chain-auxiliary group complex and a peptide thioester form (ALLH-COSR).

FIG. 21 illustrates an HPLC profile and an ESI-MS spectrum of a reaction product obtained by a ligation reaction between Fmoc-Asn (diphenacyl-sialyloligosaccharide)-Ser-COSR and Aux(SH)-Ser-COOH. Hereinafter, Aux represents an auxiliary group.

FIG. 22 illustrates LC/MS results obtained after a reaction between a peptide (H-SSTGWCGC-OH) 1 and MESNa.

FIG. 23 illustrates LC/MS results obtained after a reaction between a peptide (H-SSTGWCG-MESNa) 2 and MESNa.

FIG. 24 illustrates LC/MS results obtained after a reaction between the peptide (H-SSTGWCG-MESNa) 2 and MPAA.

FIG. 25 illustrates an ESI-MS spectrum of a peptide having a bis(2-sulfanylethyl)amino group at the C-terminal.

DESCRIPTION OF EMBODIMENTS

1. Definitions

Figure 1:
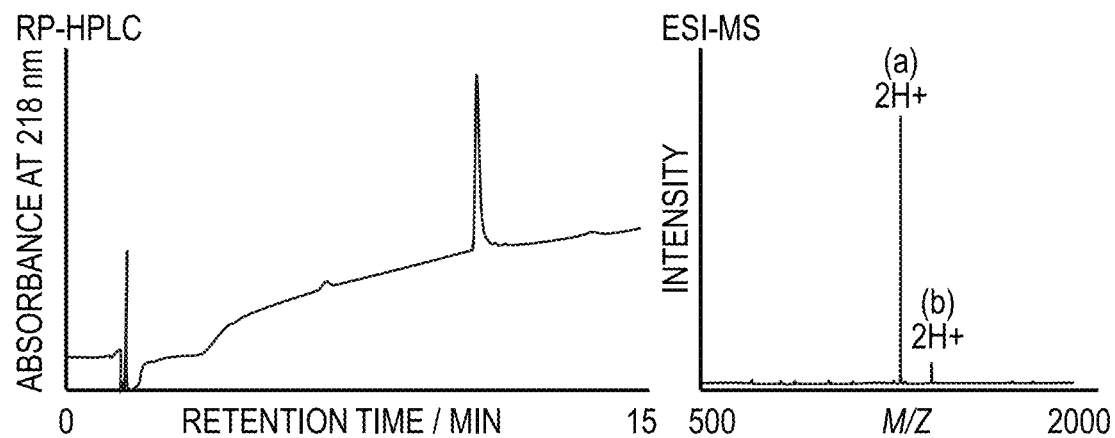
FIG. 1 illustrates an HPLC profile and an ESI-MS spectrum after purification of tert-Boc-Asn (diphenacyl-sialyloligosaccharide)-STrt.

In the present invention, the term "amino acid" is used in the broadest sense, and embraces not only natural amino acids, namely, serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro) but also unnatural amino acids such as an amino acid mutant. Accordingly, in the present invention, amino acid embraces, for example, an L-amino acid; a D-amino acid; a chemically modified amino acid; an amino acid not used as a constituting material of a protein in a living body, such as norleucine, β-alanine, and ornithine; and a mutant in which a side chain substituent of an amino acid is further substituted by another substituent (such as hydroxylysine (Hyl) or hydroxyproline (Hyp)).

In the present invention, the term "amino thioacid" refers to an amino acid in which a carboxyl group of an amino acid has been converted to a thioic acid group (—COSH), and is typically an amino acid having the following structure containing an α-amino group:

H$_2$N—CH(R)—COSH          [Formula 16]

In this compound, R represents a side chain of any amino acid, and hence R may be a side chain of a natural amino acid, or may be substituted with an unnatural side chain.

As a method for introducing a thioic acid group to a carboxyl group, various methods are known. Examples of such a method include a production method through a reaction between a carboxylic acid corresponding to a target thiocarboxylic acid and phosphorus sulfide in the presence of an antimony catalyst (such as Ph$_3$SbO) (Chem. Ber, 123, 2081-2082 (1990)), a method using hydrogen sulfide as a sulfurizing agent (J. Org. Chem., 25, 180-182 (1960)), a method in which a carboxylic acid is converted to an acid halide to be reacted with a metal salt of hydrogen sulfide (sodium salt or potassium salt) (Org. Synth., 4, 924 (1963); Synthesis., 998-1004 (2005)), a method using, as a sulfurizing agent, N,N-dimethylformthioamide or thioacetamide for an acid halide (Phosphorus, Sulfur, and Silicon., 178, 1661-1665 (2003)), and a method including conversion to a mixed acid anhydride through a reaction between chlorocarbonate and a corresponding carboxylic acid, and reaction with hydrogen sulfide (Chem. Pharm. Bull., 34, 999-1014 (1986)). In the present invention, an amino acid can be converted to a thioacid amino acid by any of these known methods to be used in the present invention. Alternatively, an amino acid derivative can be prepared by, for example, conversion of a carboxyl group of an amino acid to a thioester group, and deprotection of a protecting group of a sulfur atom.

In the present invention, an amino acid and an amino thioacid may be glycosylated or may not be glycosylated.

Herein, the term "glycosylated amino acid" refers to an amino acid to which a sugar chain is bound, and the sugar chain may be bound to the amino acid through a linker. The term "glycosylated peptide" refers to a peptide in which a sugar chain is bound in a position of an amino acid constituting the peptide, and the sugar chain may be similarly bound to the amino acid through a linker. The binding site between the sugar chain and the amino acid is not especially limited, and the amino acid preferably binds to the reducing end of the sugar chain.

The type of the amino acid to which the sugar chain is bound is not especially limited, and any one of natural amino acids and unnatural amino acids can be used. From the viewpoint that a glycosylated amino acid has the same or a similar structure as or to that present in vivo as a glycopeptide (glycoprotein), the glycosylated amino acid is preferably glycosylated Asn such as an N-linked sugar chain, glycosylated Ser and glycosylated Thr such as an O-linked sugar chain, glycosylated Hyl, or glycosylated Hyp, and is particularly preferably glycosylated Asn.

Besides, when a sugar chain and an amino acid are bound through a linker, from the viewpoint of bindability to the linker, the amino acid of the glycosylated amino acid is preferably an amino acid having two or more carboxyl groups in a molecule such as aspartic acid or glutamic acid, an amino acid having two or more nitrogen atoms in a molecule such as lysine, arginine, histidine, or tryptophan, an amino acid having a hydroxyl group in a molecule such as serine, threonine, or tyrosine, an amino acid having a thiol group in a molecule such as cysteine, or an amino acid having an amide group in a molecule such as asparagine or glutamine. In particular, from the viewpoint of reactivity, aspartic acid, glutamic acid, lysine, arginine, serine, threonine, cysteine, asparagine, and glutamine are preferred.

Herein, the term "sugar chain" refers to a compound formed by linkage of one or more unit sugars (monosaccharides and/or derivatives thereof). When two or more unit sugars are linked, the respective unit sugars are linked to one another by dehydration condensation via a glycoside bond. Examples of such a sugar chain include, but are not limited to, not only monosaccharides and polysaccharides contained in a living body (such as glucose, galactose, mannose, fucose, xylose, N-acetylglucosamine (GlcNAc), N-acetylgalactosamine (GalNAc), sialic acid, and complexes and derivatives thereof) but also a wide range of sugar chains degraded or induced from complex biomolecules such as degraded polysaccharides, glycoproteins, proteoglycans, glycosaminoglycans, and glycolipids. The sugar chain may be linear or branched.

Herein, the term "sugar chain" embraces a derivative of a sugar chain, and examples of the derivative of a sugar chain include, but are not limited to, sugar chains in which a sugar constituting the sugar chain is a sugar having a carboxyl group (such as aldonic acid in which the C-1 position has been oxidated to be a carboxylic acid (for example, D-gluconic acid obtained through oxidation of D-glucose), uronic acid in which a C atom at the terminal has been changed to a carboxylic acid (for example, D-glucuronic acid obtained through oxidation of D-glucose)), a sugar having an amino group or a derivative of an amino group (such as an acetylated amino group) (for example, N-acetyl-D-glucosamine, N-acetyl-D-galactosamine, or the like), a sugar having both an amino group and a carboxyl group (for example, N-acetylneuraminic acid (sialic acid), N-acetylmuramic acid, or the like), a deoxy sugar (for example, 2-deoxy-D-ribose), a sulfated sugar having a sulfate group, and a phosphorylated sugar having a phosphoric acid group.

A sugar chain usable in the present invention is not especially limited, and may be a sugar chain present in vivo as a complex carbohydrate (such as a glycopeptide (or a glycoprotein), a proteoglycan, or a glycolipid), or may be a sugar chain not present in vivo as a complex carbohydrate.

A sugar chain present in vivo as a complex carbohydrate is preferred from the viewpoint that a glycoamino acid or glycopeptide that can be administered to a living body can be produced. Examples of such a sugar chain include an N-linked sugar chain and an O-linked sugar chain bound to a peptide (or a protein) in vivo as a glycopeptide (or a glycoprotein). An N-linked sugar chain is preferably used. Examples of the N-linked sugar chain include a high mannose type sugar chain, a complex type sugar chain, and a hybrid type sugar chain, and a complex type sugar chain is particularly preferred.

An example of a complex type sugar chain usable in the present invention includes a sugar chain represented by the following general formula:

[Formula 17]

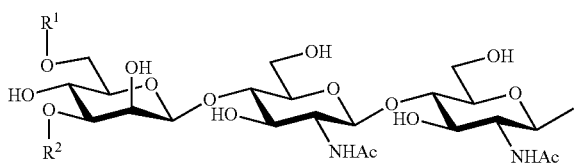

wherein $R^1$ and $R^2$ are the same or different, and represent:

[Formula 18]

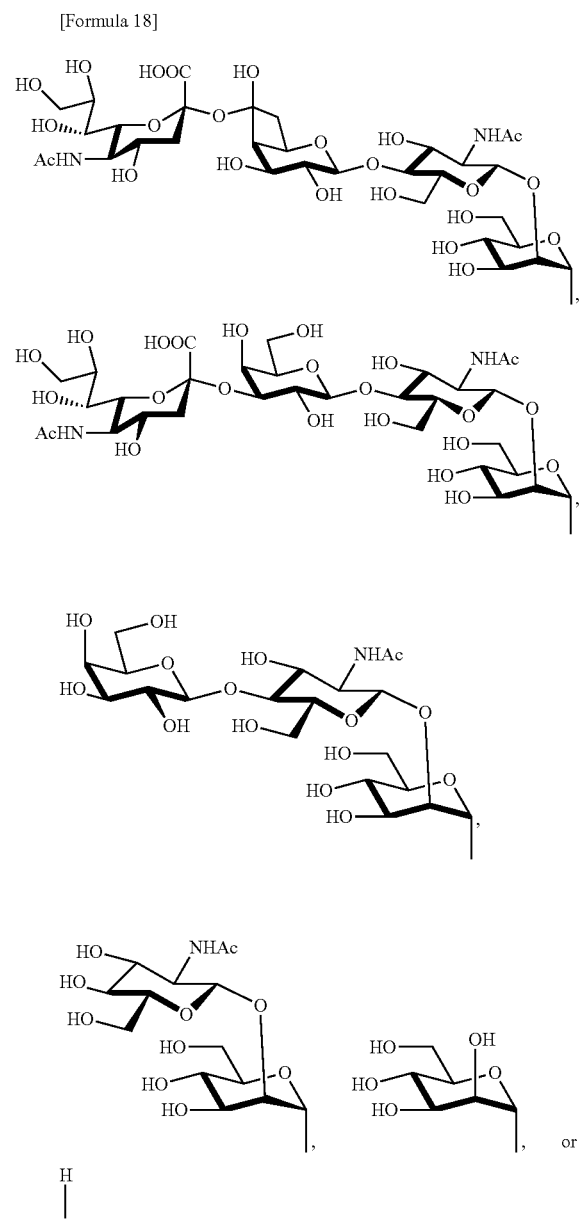

and Ac represents an acetyl group.

2. Method for Producing Peptide Thioester

In one aspect, the present invention relates to a method for producing a peptide thioester (hereinafter also referred to as the "peptide thioester production method of the present invention").

The peptide thioester production method of the present invention comprises the steps of:

(1) providing a peptide having the following sequence:

[Formula 19]

R-X-CGC-COOH—      (1)

wherein R represents any amino acid sequence; X represents any amino acid; and CGC represents any amino acid triplet of cysteine-glycine-cysteine;

(2) causing a transfer between an SH group of the C-terminal cysteine and a carbonyl group of the glycine in the CGC triplet to obtain an R-X-CG-thioester; and (3) causing, in the R-X-CG-thioester, a transfer between the SH group of the cysteine and a carbonyl group of X, and ring-closure condensation between an amino group of the cysteine and a carbonyl group of the thioester of the glycine to obtain a peptide thioester.

The step (1) is a step of providing a peptide (1) corresponding to a starting material. The peptide (1) has a target amino acid sequence to be ligated, and in the present invention, is characterized by being designed to have a CGC triplet at the C-terminal.

The peptide (1) can be produced by chemical synthesis, or a peptide produced using an expression system can be directly used. Accordingly, the present invention is advantageous in very high versatility because it can be applied to a peptide having a large size that is difficult to produce by chemical synthesis.

For producing the peptide (1) using an expression system, a method using, as a host cell, a cell of any of microorganisms such as bacterium, animals and plants can be employed. Such a method is known to those skilled in the art, and the peptide can be obtained typically by performing a step of preparing a nucleic acid molecule encoding a partial peptide to be expressed, introducing the prepared nucleic acid molecule into a host cell of an expression system, culturing and growing a transformant resulting from the introduction to express the desired partial peptide, and purifying the thus produced polypeptide chain if necessary.

As a method for preparing a nucleic acid molecule encoding a polypeptide chain to be expressed, any of methods known in the technical field can be employed. For example, a method in which a cDNA encoding a target polypeptide chain is produced, and the resultant is used as a template for performing nucleic acid amplification such as PCR using an appropriate primer can be employed. In the present invention, the nucleic acid molecule may be designed to be expressed as a peptide including the CGC triplet at the C-terminal of the target polypeptide chain, and if necessary, a purification tag (such as a His tag, a GST tag, a S tag, or a T7 tag) containing a polypeptide having bondability to a specific substance. The thus obtained nucleic acid molecule can be cloned on any of various vectors for storage. Specific vectors suitable for a prescribed host are well known to those skilled in the art, and many of these are commercially available.

In one embodiment of the present invention, the peptide (1) is a glycosylated peptide.

In the peptide thioester production method of the present invention, formation of a peptide thioester is achieved, through two stage reactions, by forming a thioester from a CGC-COOH portion at the C-terminal, and forming and stabilizing a diketopiperazine from a portion of a CG-thioester substituent formed through the first-stage reaction.

[Formula 20]

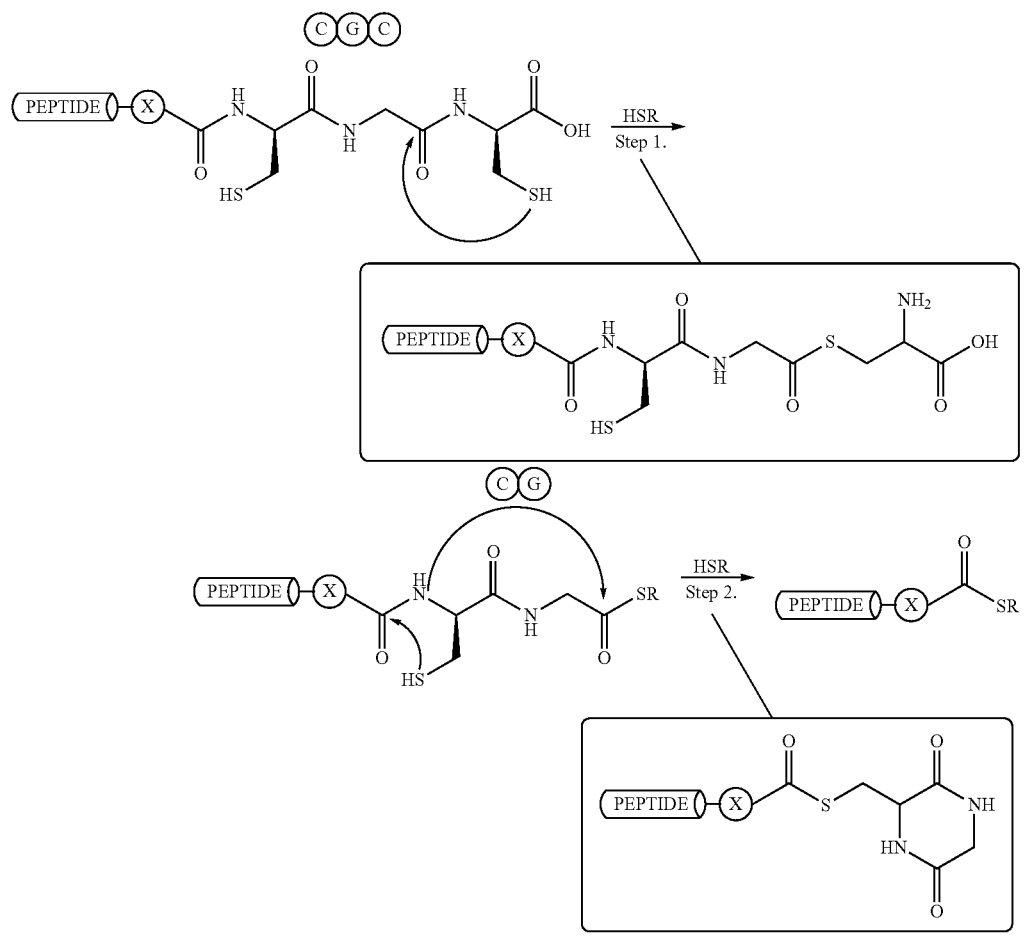

The step (2) is a step of causing, in the peptide (1), a transfer between an SH group of the C-terminal cysteine and a carbonyl group of the glycine in the CGC triplet to obtain an R-X-CG thioester (first-stage reaction).

The reaction in the step (2) can be accelerated in the presence of a given thiol. Examples of the thiol usable in the reaction in the step (2) include, but are not limited to, sodium 2-mercaptoethanesulfonate (MESNa), 2-amionethanethiol, and bis (2-sulfanylethyl) amine. One of these thiols or a combination of a plurality of these can be used.

An amount of the thiol to be used in the reaction in the step (2) can be 1 to 1000 equivalents, preferably 10 to 100 equivalents, and more preferably 15 to 30 equivalents with respect to one thiol residue in the peptide (1) used as a raw material peptide.

A solvent used in the reaction in the step (2) may be a buffer solution (a phosphate buffer, or citrate buffer), and a reaction pH is pH 1.0 to 5.0, and preferably pH 2.0 to 4.0.

A reaction temperature employed in the reaction in the step (2) is not especially limited, and the reaction can be performed in a range of 30° C. to 70° C., and is preferably performed in a range of 45° C. to 55° C. (for example, 50° C.).

A reaction time of the reaction in the step (2) can be appropriately set in a range of 1 to 120 hours, for example, 24 to 72 hours, in accordance with the amount of the peptide (1) used as the raw material peptide.

In one embodiment of the present invention, in the reaction in the step (2), sodium 2-mercaptoethanesulfonate (MESNa), 2-aminoethanethiol, or bis(2-sulfanylethyl)amine is used as the thiol. When 2-aminoethanethiol or bis(2-sulfanylethyl)amine is used in the reaction in the step (2), it can be expected to prevent reduction of the yield otherwise caused because the terminal cysteine released from the CGC triplet through the reaction in the step (2) is incorporated into the R-X-CG-thioester again.

The step (3) is a step of causing a transfer between an SH group of cysteine and a carbonyl group of X, and forming a bond between an amino group of cysteine and a carbonyl group of glycine in the R-X-CG-thioester generated as a result of the step (2), thereby generating diketopiperazine to obtain a peptide thioester (second-stage reaction).

The reaction in the step (3) can be accelerated in the presence of a given thiol. Examples of the thiol usable in the reaction in the step (3) include, but are not limited to, sodium 2-mercaptoethanesulfonate (MESNa), mercaptophenylacetic acid (MPAA), 2-mercaptopropionic acid, thiophenol, benzyl mercaptan, and ¾-mercapto-benzylsulfonate. One of these thiols, or a combination of a plurality of these can be used.

An amount of the thiol used in the reaction in the step (3) can be 1 to 1000 equivalents, preferably 10 to 100 equivalents, and more preferably 15 to 30 equivalents with respect to one thiol residue of the R-X-CG-thioester.

A solvent used in the reaction in the step (3) may be a buffer solution (a phosphate buffer, or a citrate buffer), and a reaction pH can be a more neutral or basic condition as compared with that of the step (2), such as a pH ranging from 5.0 to 13.0, a pH ranging from 6.0 to 12.0, or a pH ranging from 7.0 to 11.0.

A reaction temperature employed in the reaction of the step (2) is not especially limited, and the reaction can be performed in a range of 20° C. to 50° C., and is preferably performed in a range of 30° C. to 40° C. (for example, 37° C.).

A reaction time of the reaction in the step (3) can be appropriately set in a range of 0.5 to 12 hours, for example, 1.0 to 12 hours.

In one embodiment of the present invention, after the reaction in the step (2) and before the reaction in the step (3), the reaction product in the step (1) is purified. The purification can be performed by any method usually employed for purification of a peptide, and examples of the method to be employed include, but are not limited to, crystallization, a counter-current distribution method, partition chromatography, a gel filtration method, ion exchange chromatography, and high performance liquid chromatography (HPLC).

In the peptide thioester production method of the present invention, the type of the amino acid X linked to the CGC triplet is not especially limited, and can be any amino acid. From the viewpoint of efficient production of a peptide thioester, the type of the amino acid X is preferably appropriately changed in accordance with the type of the thiol used in the reaction in the step (3). For example, when sodium 2-mercaptoethanesulfonate (MESNa) is used in the reaction in the step (3), any one of serine, methionine and alanine is preferably used as the amino acid X. In a preferred embodiment of the present invention, when sodium 2-mercaptoethanesulfoate (MESNa) is used in the reaction in the step (3), methionine is used as the amino acid X.

3. Method for Producing Peptide

In another aspect, the present invention relates to a method for producing a peptide (hereinafter also referred to as the "peptide production method of the present invention").

The peptide production method of the present invention comprises a step of condensing:

(A) a peptide thioester; and
(B) an amino thioacid or peptide thioacid, or an amino acid or a peptide having an auxiliary group having the following structure (hereinafter also referred to as the auxiliary group of the present invention) introduced into an N-terminal thereof:

 [Formula 21]

X—C(SH)—Y wherein X represents any substituent separated by an acid treatment, a base treatment, a light irradiation treatment, or a reduction treatment; and Y represents a ketone or an aldehyde, to obtain a peptide, wherein at least some of side chains of amino acids constituting (A) and (B) is unprotected.

In the present invention, the phrase "at least some of side chains of amino acids is unprotected" means that at least some of the side chains of the amino acids is not protected by a protecting group usually used for protection of a side chain in peptide synthesis or protection of an amino group. Examples of such a protecting group include, but are not limited to, hydroxy protecting groups such as a methyl group, a tert-butyl group, a benzyl group, a benzoyl group, an acetyl (Ac) group, a trimethylsilyl (TMS) group, a triethylsilyl (TES) group, and a tert-butyldimethylsilyl (TBS or TBDMS) group; and amino protecting groups such as a 9-fluorenylmethoxycarbonyl (Fmoc) group, a t-butyloxycarbonyl (Boc) group, a benzyl group, an allyloxycarbonyl (Alloc) group, a 2,2,2-trichloroethoxycarbonyl (troc) group, an allyloxycarbonyl group, an acetyl group, and carbonate-based or amide-based protecting groups. Besides, the phrase "a part of side chains of amino acids is unprotected" refers to that at least one of side chains of amino acids constituting a peptide is unprotected, and the number does not matter.

In a preferred embodiment of the peptide production method of the present invention, all of the side chains of the amino acids constituting (A) and (B) are unprotected.

The peptide thioester of the compound (A) can be produced by a method known to those skilled in the art. For example, the C-terminal of a peptide can be thioesterified by activating a carboxylic acid at the C-terminal using PyBOP and DIPEA, and adding an excessive amount of alkyl thiol thereto. When this method is employed, in order to suppress configuration of a carbon of an amino acid at the C-terminal of the fragment, the alkyl thiol is added preferably at a low temperature, more preferably at a temperature of 10° C. to −80° C., and further preferably at a temperature of 0° C. to −40° C. Besides, the thioesterification can be performed by the Fmoc method or the Boc method described by Yamamoto et al., in J. Am. Chem. Soc. 2008, 130 (2), 501-510.

In one embodiment of the present invention, the peptide thioester of the compound (A) is the peptide thioester produced by the peptide thioester production method of the present invention.

In the peptide production method of the present invention, the auxiliary group introduced into the N-terminal of the peptide or amino acid is used for enabling formation of a sulfide bond to the peptide thioester and an S—N acyl transfer subsequently caused. Accordingly, it is presumed that not only the auxiliary group of the present invention but also any compound having a thiol group (—SH) in the α-, β- or γ-position can be similarly used.

The substituent X in the auxiliary group of the present invention is a substituent that can be separated by a separation treatment performed at any stage after the formation of a sulfide bond to the peptide thioester and formation of an amide bond by the S—N transfer subsequently caused. An example of the acid treatment employed for the separation treatment includes a treatment with trifluoroacetic acid (for example, a treatment performed in 0 to 95% TFA for 1 to 3 hours at room temperature under a condition of a reaction concentration of 0.1 to 1 M). An example of the base treatment employed for the separation treatment includes a treatment with phosphine/morpholine (for example, a treatment performed in a buffer (pH 8.8) using 0.3 M TCEP (tris(2-carboxyethyl)phosphine) and 1.2 M morpholine at 40° C. for 3 hours). An example of the light irradiation treatment employed for the separation treatment includes a treatment performed at a wavelength of 300 nm or more (for example, a treatment of irradiating a solution of peptide in water or water/acetonitrile (3:7) (0.5 to 1 mM)+TCEP (1 equivalent) with UV of 425 to 365 nm at room temperature for 30 minutes). An example of the reduction treatment employed for the separation treatment includes a treatment with zinc/acetic acid (for example, a treatment of adding a zinc powder (10 to 50 equivalents with respect to the auxiliary group) to a solution of a peptide in acetic acid (about 0.2 to 1 M), and stirring the resultant at 40° C. for 30 to 120 minutes).

The auxiliary group of the present invention is, in a preferred embodiment, a compound in which X is aryl.

In the peptide production method of the present invention, the introduction of the auxiliary group of the present invention into the N-terminal of an amino acid or peptide can be performed by a method known to those skilled in the art. For example, the introduction of the auxiliary group of the present invention into the N-terminal of an amino acid or peptide can be performed by utilizing reductive amination between an amino group of the amino acid and a ketone or aldehyde of the auxiliary group. The reductive amination can be accelerated by using a reducing agent usually used by those skilled in the art. Examples of the reducing agent usable in the present invention include, but are not limited to, formic acid, sodium borohydride, sodium cyanoborohydride, sodium triacetoxyborohydride, and 2-picoline-borane. One of these reducing agents, or a combination of a plurality of these can be used.

In the reductive amination, any of solvents including alkanes such as hexane, aromatic compounds such as toluene, ethers such as diethyl ether, tetrahydrofuran and dimethoxyethane, esters such as ethyl acetate, alcohols such as isopropanol, and polar solvents such as N,N-dimethylformamide can be used. Besides, a reaction time may be varied depending on the type or form (for example, whether or not it has a sugar chain) of the amino acid to be introduced, and the like, and can be 1 to 24 hours (for example, 16 hours).

In introducing the auxiliary group into the amino acid or peptide, a thiol group of the auxiliary group is preferably protected. For protecting the thiol group, any of, but not limited to, an acetyl group, a pivaloyl group, a trityl group, a trichloroacetyl group, a benzoyl group, a ferrocenoyl group, a 2,4,6-triisopropyl group, a dimethylphenylacetyl group, a 2-methoxyisobutyryl group, and a tert-butoxycarbonyl group can be used.

A condensation reaction of the compounds (A) and (B) is caused to proceed by causing the S—N acyl transfer between the peptide thioester and a thiol group of the amino thioacid or peptide thioacid, or between the peptide thioester and a thiol group of the auxiliary group of the present invention.

The condensation reaction of the compounds (A) and (B) can be performed in the presence of an acid if necessary. Examples of the acid usable in the peptide production method of the present invention include, but are not limited to, inorganic acids such as sulfuric acid, Lewis acids such as boron trifluoride diethyl ether (BF3·OEt2), dimethyl(methylthio)sulfonium trifluoromethanesulfonate (DMTST), trimethylsilyl trifluoromethanesulfonate, triethylsilyl trifluoromethanesulfonate, tripropylsilyl trifluoromethanesulfonate, dimethylethylsilyl trifluoromethanesulfonate, tribenzylsilyl trifluoromethanesulfonate, trinaphthylsilyl trifluoromethanesulfonate or tribenzylmethylsilyl trifluoromethanesulfonate, silver trifluoromethanesulfonate, cyclopentadienyl hafnium chloride, cyclopentadienyl zirconium chloride, and tin chloride, and organic acids such as formic acid, acetic acid, trifluoroacetic acid, trifluoroacetic anhydride, trifluoromethanesulfonic acid, and tetrafluoromethanesulfonic acid. One of these acids can be used, or two or more of these can be used together. Besides, an amount of the acid to be used can be appropriately set by those skilled in the art in accordance with the amount of the peptide thioester to be used.

A solvent to be used in the condensation reaction is not limited as long as it is a solvent inert to the reaction. Examples include aliphatic hydrocarbons such as hexane, heptane, and pentane, alicyclic hydrocarbons such as cyclohexane, aromatic hydrocarbons such as benzene, toluene, and xylene, halogenated hydrocarbons such as dichloromethane, chloroform, 1,2-dichloroethane, 1,1,1-trichloroethane, tetrachloroethylene, trichloroethylene, carbon tetrachloride, chlorobenzene, and o-dichlorobenzene, ethers such as diethyl ether, isopropyl ether, tetrahydrofuran, dioxane, and monoglyme, amides such as N,N-dimethylformamide, N,N-dimethylacetamide, and 1,3-dimethylimidazolidinone, sulfoxides such as dimethylsulfoxide, nitriles such as acetonitrile and propanenitrile, and mixed solvents of these.

A temperature employed in the condensation reaction can be in a range of $-80°$ C. to $40°$ C., for example, $-40°$ C. to $25°$ C.

The peptide production method of the present invention is based on the following novel finding: When an amino thioacid or peptide thioacid, or an amino acid or peptide having a specific structure at the N-terminal is used as an amino acid or a peptide for ligation to a peptide thioester, even if an unprotected amino acid is present in any of amino acid side chains of these, a thioester portion (—COSR) of the peptide thioester and a thioic acid group (—COSH) of the amino thioacid, the peptide thioacid or the auxiliary group can be selectively linked to each other. In other words, the peptide production method of the present invention has an advantage that a target peptide having a controlled structure can be produced even if repetition of protection and deprotection of an amino acid side chain and condensation is avoided. Besides, when a peptide to be produced is a glycosylated peptide, since the repetition of protection and deprotection of an amino acid side chain and condensation can be avoided, a total yield of the resultant glycosylated peptide can be increased.

The peptide production method of the present invention is, in one embodiment, a method for producing a glycosylated peptide.

Accordingly, in one embodiment of the peptide production method of the present invention, a glycosylated peptide thioester is used as the compound (A).

In another embodiment of the peptide production method of the present invention, a glycosylated amino thioacid is used as the compound (B).

In still another embodiment of the peptide production method of the present invention, a glycosylated peptide thioacid is used as the compound (B).

In still another embodiment of the peptide production method of the present invention, a glycosylated amino acid or glycosylated peptide having the auxiliary group of the present invention introduced into the N-terminal is used as the compound (B).

When the peptide production method of the present invention is applied to a method for producing a glycosylated peptide, some or all of (A) sugar chains present in the glycosylated peptide thioester, or (B) sugar chains present in the glycosylated amino thioacid or glycosylated peptide thioacid, or the glycosylated amino acid or glycosylated peptide having the auxiliary group of the present invention at the N-terminal may be, or may not be protected by a protecting group known to those skilled in the art. When a sugar chain contained in these compounds has a portion having high sensitivity to an acid (such as a sialic acid portion), a protecting group is preferably introduced into such a sugar chain portion before the condensation reaction of the compounds (A) and (B). Examples of the protecting group for a sugar chain usable in the present invention include, but are not limited to, a phenacyl group, a benzyl group, and a methyl group.

In the peptide production method of the present invention, when a glycosylated peptide thioester is used as the compound (A), the glycosylated peptide thioester can be produced by, for example, condensing a peptide thioester and a glycosylated amino thioacid to introduce a sugar chain, and by further thioesterifying the C-terminal of the resultant.

The glycosylated amino thioacid may be produced by introducing a thioic acid group into the C-terminal of a glycosylated amino acid prepared by an ordinary method, such as glycosylated asparagine (Asn), glycosylated serine (Ser), glycosylated threonine (Thr), glycosylated hydroxylysine (Hyl), or glycosylated hydroxyproline (Hyp)

Besides, in the peptide production method of the present invention, when a glycosylated peptide thioacid is used as the compound (B), the glycosylated peptide thioacid can be produced by, for example, reacting a glycosylated amino thioacid with a peptide having, at the N-terminal, a cysteine having, in a side chain thereof, a modifying group capable of forming a disulfide bond to a thioic acid group (—COSH) contained in the glycosylated amino thioacid to introduce the thioic acid group into the C-terminal of a peptide resulting from the reaction. The modifying group usable for this purpose can be easily designed by those skilled in the art. Specifically, the modifying group may be designed to be separated in forming a disulfide bond to the thioic acid group (—COSH) of the glycosylated amino thioacid. Specific examples of such a modifying group include the following Npys/Pys modifying groups (for example, Liu, C. et al., Tetrahedron Letters, 1996, 37, 933-936).

[Formula 22]

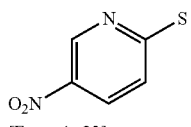

[Formula 23]

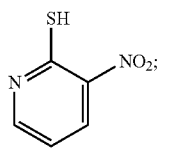 and

[Formula 24]

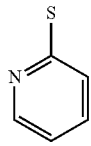

Besides, in the peptide production method of the present invention, when a glycosylated peptide having the auxiliary group of the present invention introduced into the N-terminal is used as the compound (B), the glycosylated peptide can be produced by, for example, producing a glycosylated amino thioacid having the protecting group of the present invention by introducing a thioic acid group (—COSH) to the C-terminal of a glycosylated amino acid having the auxiliary group of the present invention introduced into the N-terminal thereof, and reacting the resultant with a peptide having, at the N-terminal, a cysteine having, in a side chain thereof, a modifying group capable of forming a disulfide bond to a thioic acid group (—COSH) contained in a glycosylated amino thioacid.

In one embodiment of the present invention, the "glycosylated amino acid having the auxiliary group of the present invention introduced into the N-terminal" is a glycosylated amino acid having the following structure:

[Formula 25]

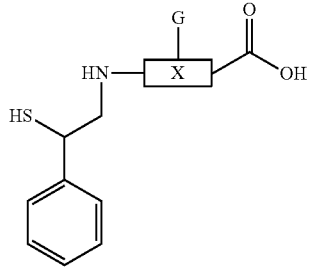

wherein X represents any amino acid, and G represents any sugar chain.

In the glycosylated amino acid, X is preferably Asn, Ser, Thr, or Hyl.

In the glycosylated amino acid, a thiol group (—SH) may be or may not be protected.

In the glycosylated amino acid, a sugar chain of a side chain may be or may not be protected.

In one embodiment of the present invention, the "glycosylated amino acid having the auxiliary group of the present invention introduced into the N-terminal" is a glycosylated dipeptide having the following structure:

[Formula 26]

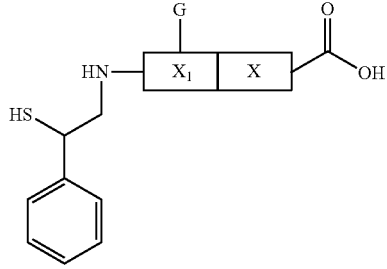

wherein $X_1$ represents Asn, Ser, Thr, or Hyl, X represents any amino acid, and G represents any sugar chain.

In the glycosylated dipeptide, a thiol group (—SH) may be or may not be protected.

In the glycosylated dipeptide, a sugar chain of a side chain may be or may not be protected.

It is noted that terms used herein are used for describing specific embodiments and are not intended to limit the invention.

Besides, the term "to include", "to contain" or "to comprise" is used to intend that a mentioned item (such as a member, a step, an element, or a numerical value) exists except that it should be understood differently contextually, and does not exclude existence of another item (such as a member, a step, an element, or a numerical value).

Unless otherwise defined, all the terms used herein (including technical terms and scientific terms) have the same meanings as those widely understood by those skilled in the art of the technology to which the present invention belongs. The terms used herein should be construed in meanings consistent with their meanings employed in the present specification and the field of the related art unless different definition is given, and should not be construed in ideal or excessively formal meanings.

Terms "first", "second" and the like may be used to express various types of elements in some cases, and it should be understood that these elements are not limited by these terms. These terms are used merely for distinguishing one element from another, and for example, a first element can be described as a second element, and similarly, a first element can be described as a second element without departing from the scope of the present invention.

Now, the present invention will be described more specifically with reference to examples, and it is noted that the present invention can be embodied in various embodiments and should not be construed to be limited to the examples herein described.

EXAMPLES

[Example 1] Synthesis of Glycopeptide Using Amino Thioacid (1) Synthesis of Glycosylated Amino Thioacid (1-1) Synthesis of Tert-Boc-Asn (Diphenacyl-Sialyloligosaccharide)-STrt

[Formula 27]

Boc-Asn (diphenacyl-sialyloligosaccharide)-OH (18.0 mg, 6.7 μmol) (Murakami, M.; Kiuchi, T.; Nishihara, M.; Tezuka, K.; Okamoto, R.; Izumi, M.; Kajihara, Y., Chemical synthesis of erythropoietin glycoforms for insights into the relationship between glycosylation pattern and bioactivity, Science Advances. 2016) was dissolved in DMF (486.0 μL), and triphenylmethanethiol (47.2 mg, 0.17 mmol), PyBOP (29.5 mg, 56.6 μmol), and DIEA (10.0 μL, 57.3 μmol) were further added thereto at −15° C. under an Ar atmosphere, followed by stirring. After performing a reaction for 15 hours, cooled $Et_2O$ (20 mL) was added to the resultant, and the thus obtained white suspension solution was centrifuged to collect a precipitate. The obtained precipitate was purified under the following conditions: HPLC (Capcell Pak C18 φ10×250 mm, 15 mM ammonium acetate aqueous solution: $CH_2CN$=65:35 to 20:80, 80 min, flow rate: 3 mL/min). After the purification, a desalination treatment was performed using a strong acid cation exchange column of Dowex resin, and the resultant was freeze dried to finally obtain a white solid of tert-Boc-Asn (diphenacyl-sialyloligosaccharide)-STrt (11 mg, 57%) (FIGS. 1 and 2): m/z calcd. for $C_{128}H_{178}N_8O_{67}S$: $[M+2H]^{2+}$ 1467. 4, found for $[M+2H]^{2+}$ 1467.1 regarding (a), $C_{19}H_{164}N_8O_{67}S$: $[M+2H]^{2+}$ 1346.3, found for $[M+2H]^{2+}$ 1346.1 regarding (b).

Figure 2:
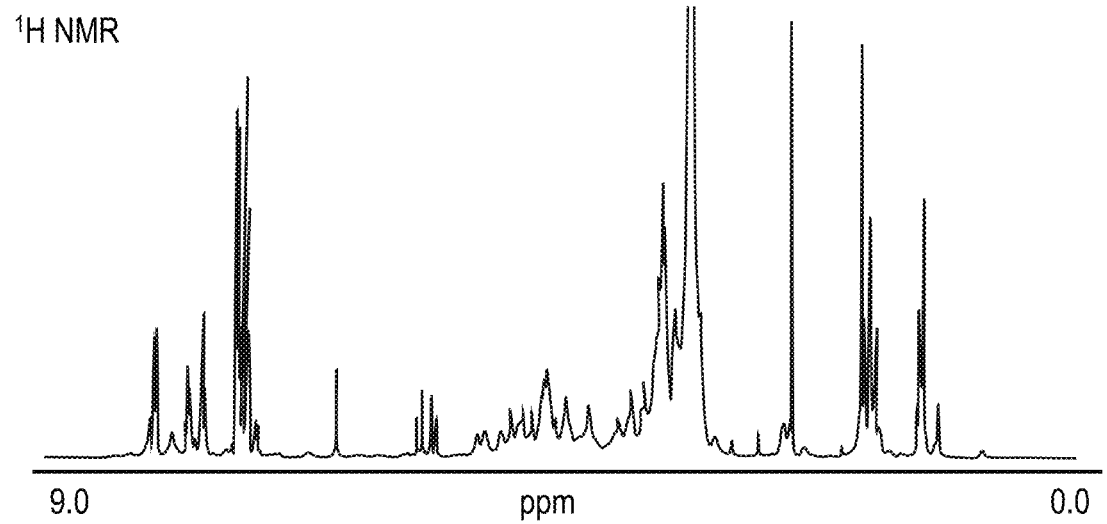
FIG. 2 illustrates an NMR spectrum after purification of tert-Boc-Asn (diphenacyl-sialyloligosaccharide)-STrt.

In FIG. 1, a compound (b) is Boc-Asn (diphenacyl-sialyloligosaccharide)-STrt 1, and a compound (a) is Boc-Asn (diphenacyl-sialyloligosaccharide)-SH resulting from release of the STrt group in an ESI-MS device.

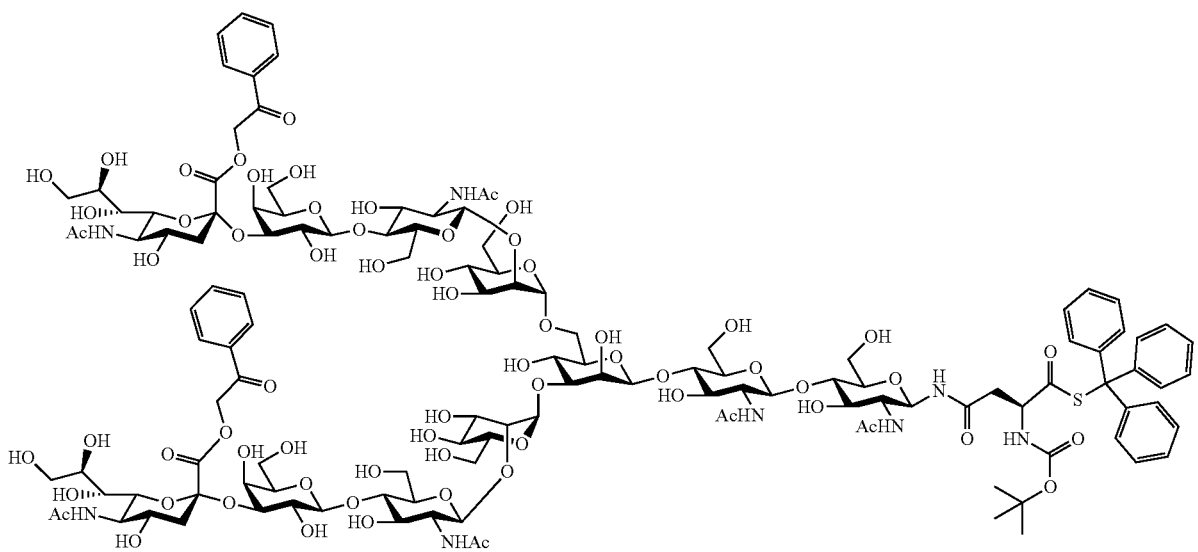

(1-2) Synthesis of H-Asn (diphenacyl-sialyloligosaccharide)-SH

[Formula 28]

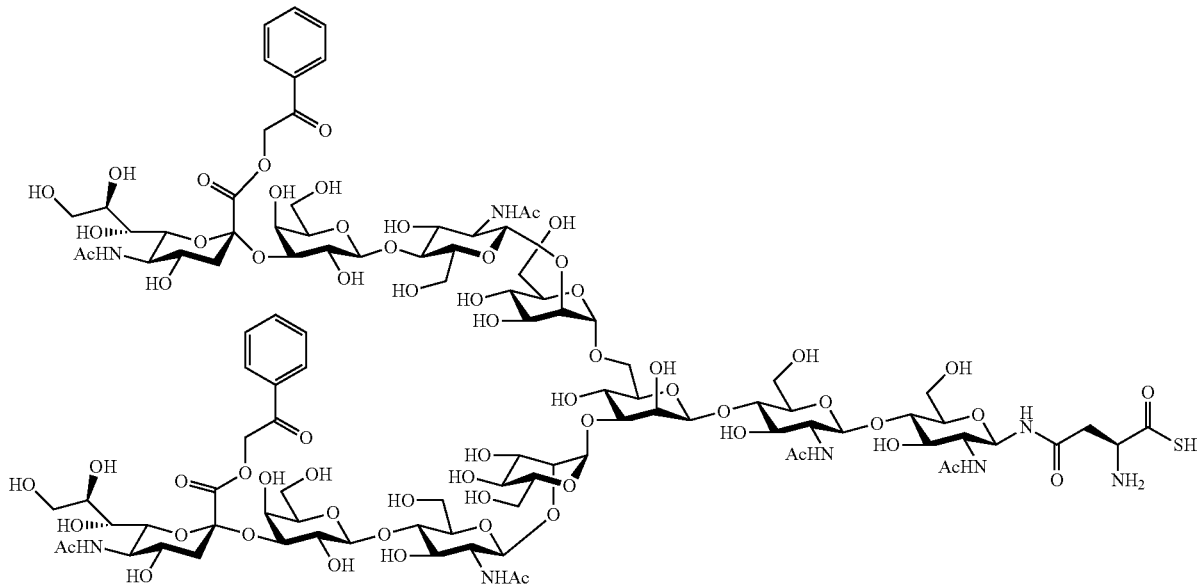

Figure 3:
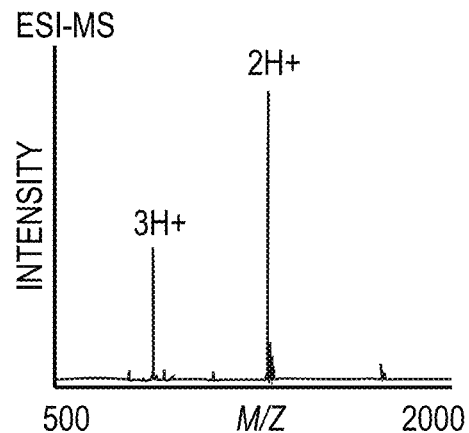
FIG. 3 illustrates an ESI-MS spectrum after purification of H-Asn (diphenacyl-sialyloligosaccharide)-SH.
Figure 4:
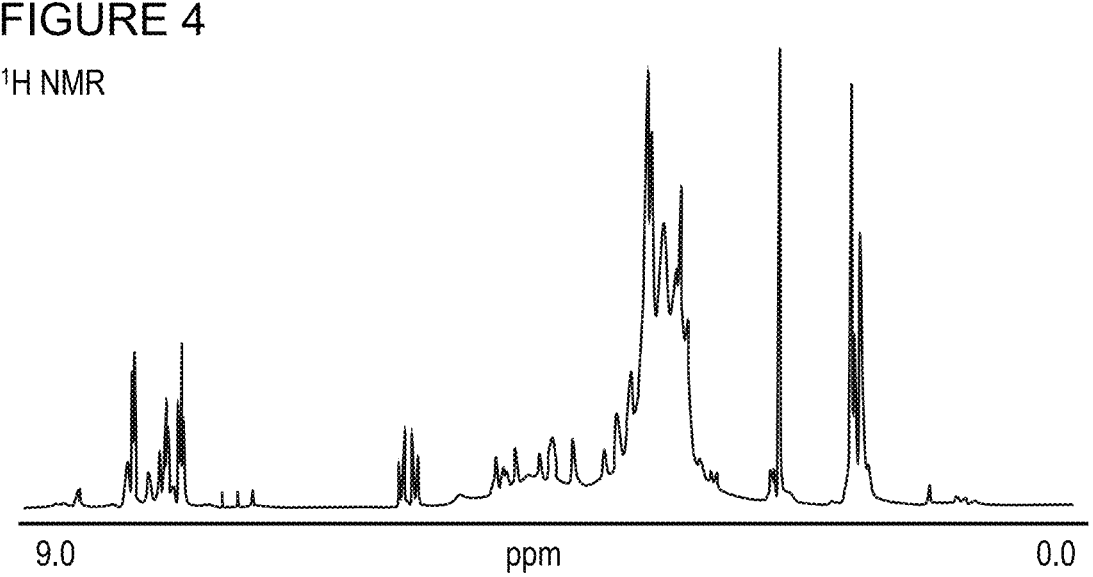
FIG. 4 illustrates an NMR spectrum after purification of H-Asn (diphenacyl-sialyloligosaccharide)-SH.

To the thus obtained Boc-Asn (diphenacyl-sialyloligosaccharide)-STrt 1 (8.5 mg, 2.9 μmol), 750 μL of TFA containing TIPS (5%, v/v) was added, followed by stirring at room temperature. Reaction tracking was performed by TLC, and after performing the reaction for 30 minutes, cooled Et$_2$O(10 mL) was added thereto, and the thus obtained white suspension solution was centrifuged. This operation was performed twice, the resultant precipitate was dissolved in a 0.1% TFA aqueous solution, and the resultant was freeze dried to finally obtain a white solid of H-Asn (diphenacyl-sialyloligosaccharide)-SH (6.9 mg, 92%) (FIGS. 3 and 4): ESI-MS: m/z calcd. For (a) C$_{104}$H$_{156}$N$_8$O$_{65}$S: [M+2H]$^{2+}$ 1296.2, [M+3H]$^{3+}$ 864.5, found for [M+2H]$^{2+}$ 1296.5, [M+3H]$^{3+}$+864.7.

(1-3) Synthesis of tert-Boc-Asn (asialo oligosaccharide)-STrt

[Formula 29]

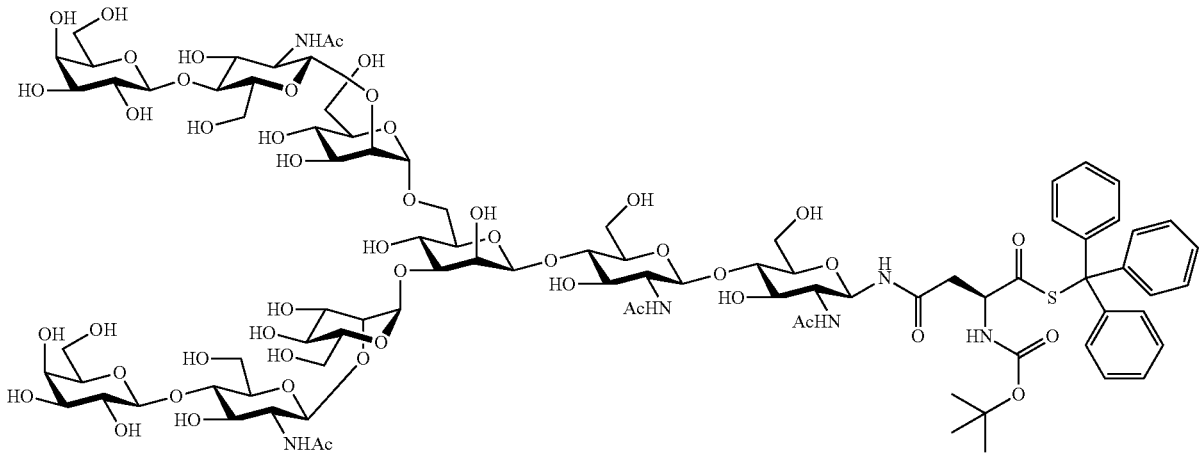

Boc-Asn (asialo oligosaccharide)-OH (10.0 mg, 5.4 mol) was dissolved in DMF (250.0 μL), and triphenylmethanethiol (44.5 mg, 0.16 mmol), PyBOP (17.0 mg, 32.6 μmol), and DIEA (6.0 μL, 34.4 μmol) were further added thereto at −15° C. under an Ar atmosphere, followed by stirring. After performing the reaction for 1.5 hours, cooled Et$_2$O (40 mL) was added to the resultant, and the thus obtained white suspension solution was centrifuged to collect a precipitate. The obtained precipitate was purified under the following conditions: HPLC (CAPCELL PAK C18 φ10×250 mm, 0.1% formic acid aqueous solution: 0.1% solution of formic acid in CH$_2$CN=80:20 to 40:60, 45 min, flow rate: 3 mL/min).

Figure 5:
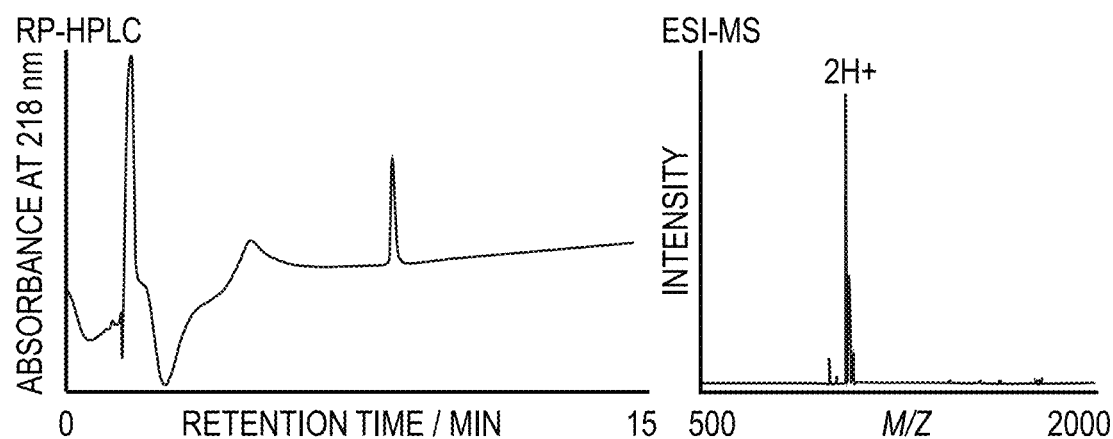
FIG. 5 illustrates an HPLC profile and an ESI-MS spectrum after purification of tert-Boc-Asn (asialo oligosaccharide)-STrt.

Finally, a white solid of tert-Boc-Asn (asialo oligosaccharide)-STrt 3 (6.7 mg, 59%) was obtained (FIG. 5): m/z calcd. for $C_{71}H_{118}N_6O_{49}S$: $[M+2H]^{2−}$ 936.8, found for $[M+2H]^{2+}$ 936.5. It is noted that the observed MS corresponds to Boc-Asn (asialo oligosaccharide)-SH resulting from release of the STrt group in the ESI-MS device.

(1-4) Synthesis of H-Asn (asialo oligosaccharide)-SH

[Formula 30]

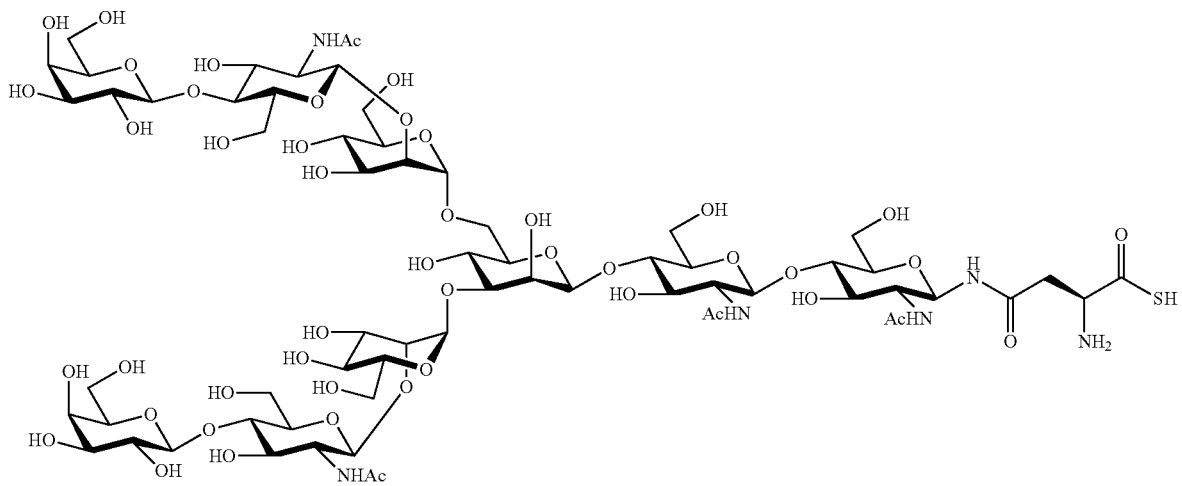

To the thus obtained Boc-Asn (asialo oligosaccharide)-STrt 3 (2.0 mg, 0.95 μmol), 65.0 μL of TFA containing TIPS (5%, v/v) was added, followed by stirring at room temperature. Reaction tracking was performed by TLC, and after performing the reaction for 30 minutes, cooled Et$_2$O (10 mL) was added thereto, followed by stirring. The thus obtained white suspension solution was centrifuged to collect a white precipitate. An operation of adding cooled Et$_2$O (10 mL) to the precipitate, stirring the resultant, and centrifuging the thus generated white suspension solution was further performed twice. The resultant precipitate was dissolved in a 0.1% TFA solution, and the resultant was freeze dried to obtain a white solid of H-Asn (asialo oligosaccharide)-SH 4 (0.6 mg, 34%).

(2) Synthesis of Amino Thioacid (2-1) Synthesis of Boc-Leu-STrt

[Formula 31]

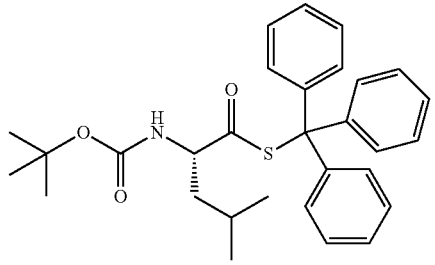

Figure 6:
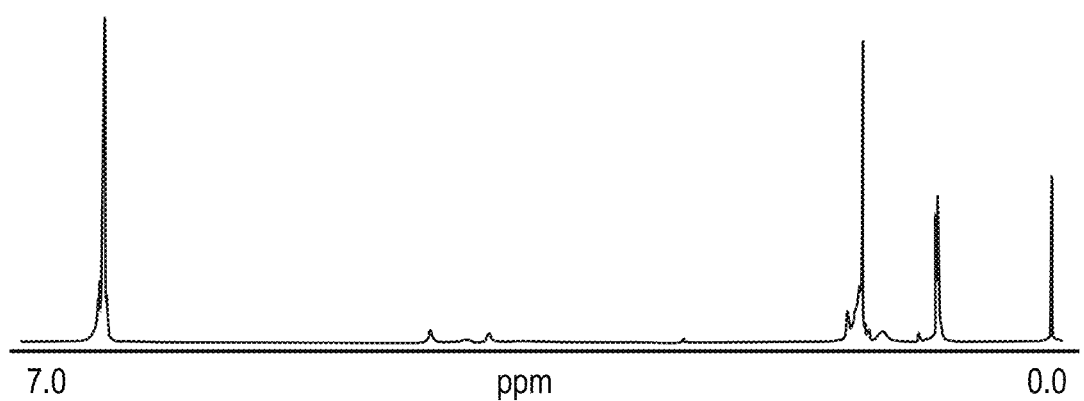
FIG. 6 illustrates an NMR spectrum after purification of Boc-Leu-STrt.

Boc-Leu-OH (301 mg, 1.21 mmol), triphenylmethanethiol (684 mg, 2.47 mmol), and PyBOP (1.25 g, 2.40 mmol) were dissolved in dry DCM (12.0 mL), and the resultant was allowed to stand still at −20° C. under an Ar atmosphere. To the resultant solution, DIEA (419 μL, 2.40 mmol) was added, followed by stirring for 1.5 hours. The resultant was separated using a saturated ammonium chloride aqueous solution, and the organic layer was concentrated under reduced pressure. The thus obtained pale yellow solid was dissolved in a small amount of DCM, and purified by silica gel column chromatography (ethyl acetate/hexane=1:8) to finally obtain a white powder of Boc-Leu-STrt 5 (301 mg, 51%) (FIG. 6).

(2-2) Synthesis of H-Leu-SH

[Formula 32]

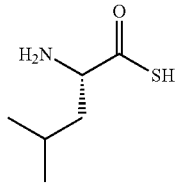

Figure 7:
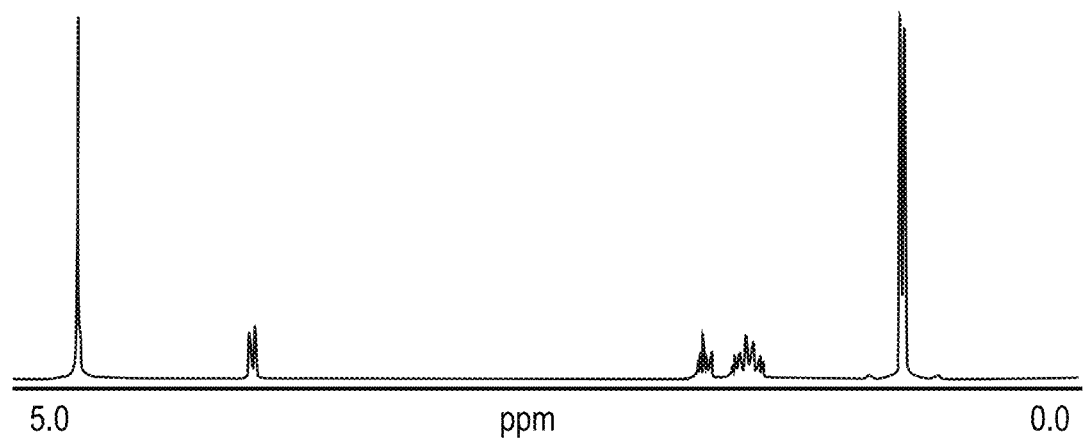
FIG. 7 illustrates an NMR spectrum after purification of H-Leu-SH.

To the thus obtained Boc-Leu-STrt 5 (50 mg, 102 µmol), 5.0 mL of TFA containing TIPS (5%, v/v) was added, followed by stirring at room temperature for 30 minutes. TFA was removed under reduced pressure, and 40 mL of cooled $Et_2O$ was immediately added thereto. The thus obtained white suspension solution was centrifuged to obtain a white precipitate. An operation of adding 40 mL of cooled $Et_2O$ to the white precipitate and centrifuging the resultant was further performed twice in total. The thus obtained white precipitate was dissolved in a 0.1% TFA aqueous solution, and the resultant was freeze dried to obtain a white powder of H-Leu-SH 6 (12.4 mg, 83%) (FIG. 7).

The following amino thioacids having different side chains were synthesized by similar methods:

[Formula 33]

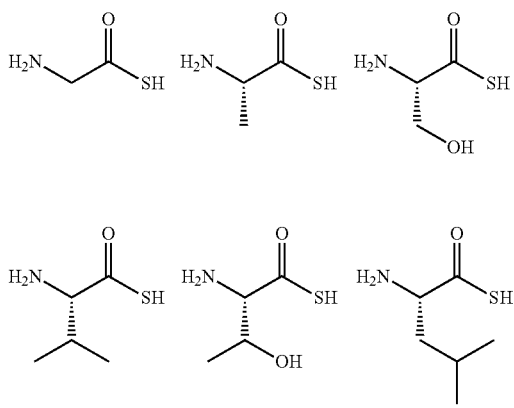

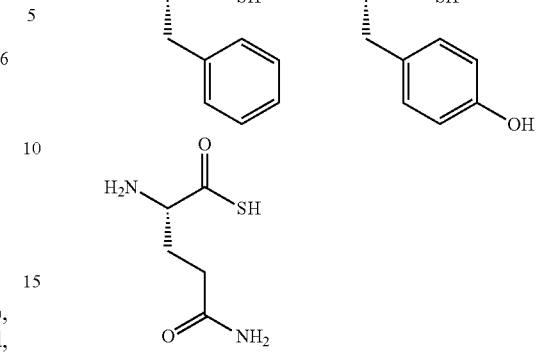

(3) Procedures for Synthesis of Fmoc Solid Phase Peptide (SPPS)

(3-1) Synthesis of Peptide Thioester

[Formula 34]

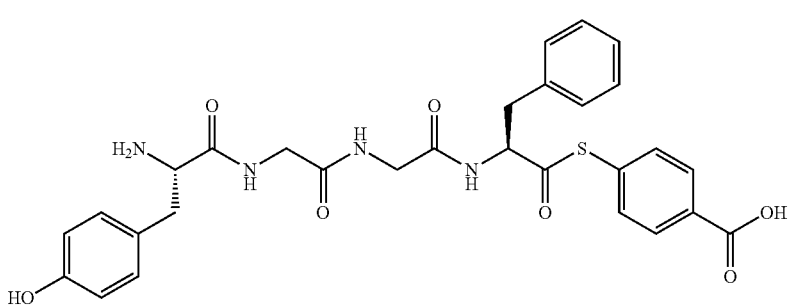

Figure 8:
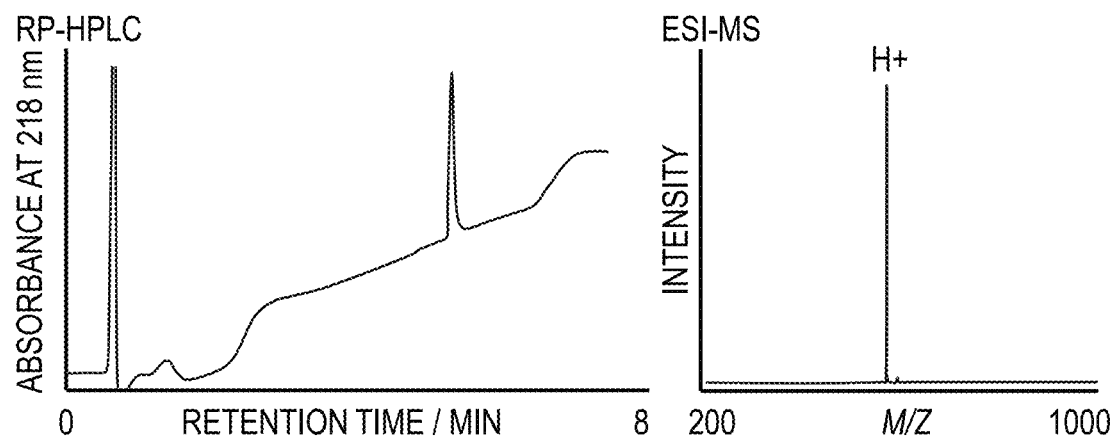
FIG. 8 illustrates an HPLC profile and an ESI-MS spectrum after purification of a peptide-thioester 7.

Fmoc-amino acids used were Gly, Tyr, and Phe. For peptide-α-thioester 7, Fmoc SPPS protocol using Dawson AM resin as a resin was employed. The first Fmoc-amino acid (Fmoc-Phe, 0.84 mmol) was activated in DMF (3.0 mL) for 1 minute with HBTU (314 mg, 0.84 mmol), HOBt (114 mg, 0.84 mmol) and DIEA (219 µL, 0.84 mmool), the resultant was added to the resin (141 mol) in an SPPS tube, and the resultant reaction solution was stirred at room temperature for 45 minutes. Condensation of the other Fmoc amino acids were performed in a similar manner to that described above. Besides, deprotection of the Fmoc group was performed by adding DMF containing piperidine (20%, v/v) to the resin, stirring the resultant for 10 minutes, and washing the resultant with DMF. After the condensation of the last residue, the Fmoc group was deprotected, and the resultant resin was washed with DMF and DCM. Furthermore, in order to cut a peptide out of the resin, 2.4 mL of TFA containing TIPS (5%, v/v) was added to the resin, followed by stirring at room temperature for 1 hour. To the thus obtained solution, cooled $Et_2O$ (40 mL) was added, and the resultant was centrifuged to collect a white precipitate. The same operation was performed twice, and the resultant was freeze dried to obtain a yellow solid of H-Tyr-Gly-Gly-Phe-DBz. The thus obtained H-Tyr-Gly-Gly-Phe-DBz (7.0 mg, 13 µmol) was dissolved in 1.3 mL of phosphate buffer (pH 3.7), and a 1.0 M $NaNO_2$ aqueous solution (130 µL, 130

μmol) was added thereto at a constant temperature of −5° C. After stirring the resultant reaction solution for 2 minutes, 1.3 mL of phosphate buffer (pH 7.0) containing 4-mercaptobenzoic acid (20.0 mg, 129 μmol) dissolved therein was added to the reaction solution. The resultant was stirred for 10 minutes, cooled Et$_2$O (10 mL) was immediately added thereto, and the resultant was centrifuged. The same operation was performed twice, the aqueous phase was collected to be purified under the following conditions: HPLC (Proteonavi C8 φ10×250 mm, 0.1% formic acid aqueous solution: 0.1% solution of formic acid in CH$_2$CN=90:10 to 50:50, 80 minutes, flow rate: 3 mL/min). The thus obtained purified solution was freeze dried to obtain a yellow powder of peptide thioester 7 (2.3 mg) (FIG. 8): m/z calcd. for C$_{29}$H$_{30}$N$_4$O$_7$S: [M+H]$^+$ 579.2, found for [M+H]$^+$ 579.2.

(3-2) Synthesis of Cys-modified Peptide

[Formula 35]

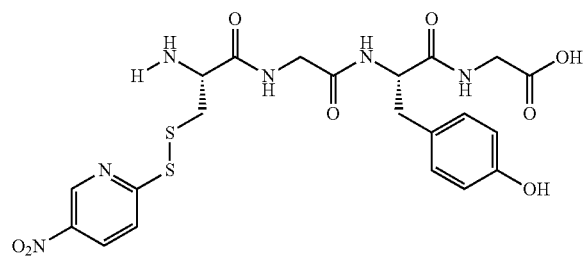

8

Fmoc-amino acids used are Gly, Tyr, and Cys (S$^t$Bu). Besides, a portion having the following structure in the above-described structure will be hereinafter referred to as Npys.

[Formula 36]

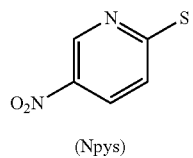

(Npys)

Figure 9:
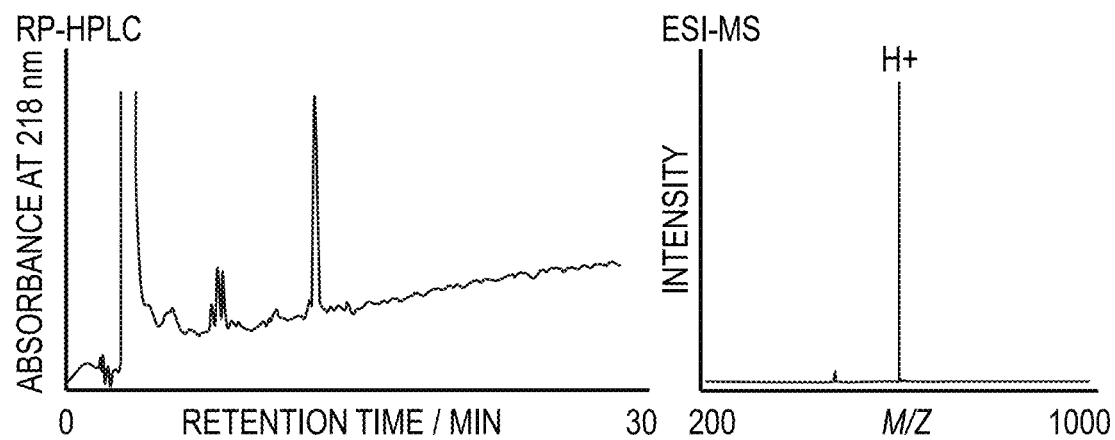
FIG. 9 illustrates an HPLC profile and an ESI-MS spectrum of H-Cys(Npys)-Gly-Tyr-Gly-OH.

Peptide 8 was synthesized by Fmoc SPPS protocol using Barlos Resin (60 μmol) as a resin. A basic condensation reaction of the amino acids was performed through similar procedures to those employed in the synthesis of the peptide thioester 7. After condensing the last residue, the Fmoc group was deprotected, and the resultant was washed with DMF. Next, in order to release tert-butanethiol of the cysteine, 2.0 mL of DMF containing 2-mercaptoethanol (20%, v/v) was added to the resin in an SPPS tube. After stirring at room temperature for 5 hours, the resultant was washed with DMF and DCM. Furthermore, in order to form a disulfide bond to Npys, 3 mL of DMF containing 2,2′-dithiobis(5-nitropyridine) (189.2 mg, 610 μmol) was added to the resin, followed by stirring at room temperature for 18 hours. The resultant was further washed with DMF and DCM, and in order to cut a peptide out of the resin, 2.0 mL of TFA containing TIPS (5%, v/v) was added thereto, followed by stirring for 3 hours. To the thus obtained solution, cooled Et$_2$O (40 mL) was added, and the resultant was centrifuged to collect a yellow precipitate. A similar operation was performed twice, and the resultant was freeze dried to obtain a yellow solid of H-Cys(Npys)-Gly-Tyr-Gly-OH (FIG. 9): m/z calcd. for C$_{21}$H$_{24}$N$_6$O$_8$S$_2$: [M+H]$^+$ 553.1, found for [M+H]$^+$ 553.4.

(4) General Reaction Procedures of Thioanhydride Ligation

The peptide thioester 7 (0.5 to 2.0 equivalents) and DIEA (5.0 to 10.0 equivalents) were added to the synthesized amino thioacid, and the resultant was reacted at room temperature under an Ar atmosphere. The reaction can be caused to efficiently proceed by setting the amino thioacid in the reaction solution to 10 to 30 mM. Reaction tracking was performed by reverse phase HPLC. The reaction is usually completed in 3 to 6 hours in using any substrate.

Coupling of Peptide Thioester and Amino Thioacid

[Formula 37]

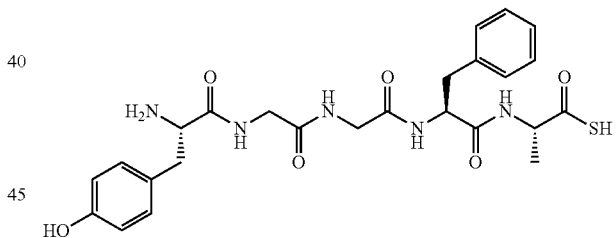

9

Figure 10:
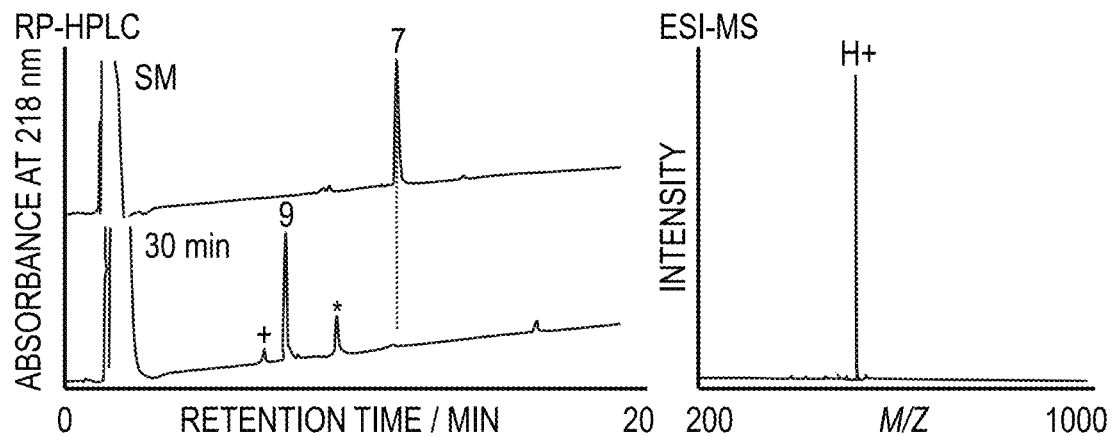
FIG. 10 illustrates an HPLC profile and an ESI-MS spectrum of a reaction product of thioanhydride ligation using alanine thioacid: A starting material, the peptide thioester 7, was present at time 0, and after performing coupling for 30 minutes, a target product of H-YGGFA-SH 9 was synthesized. A reference sign * refers to a free thiol cleaved from a peptide thioester, and a reference sign+refers to H-YGGF-SH.

The peptide thioester 7 (0.18 mg, 0.31 μmol) was dissolved in 10.0 μL of DIEA (320 mM)-containing DMF under an Ar atmosphere. H-Ala-SH (0.12 mg, 1.1 μmol) was further added thereto. The reaction converged in 30 minutes. Reaction tracking was performed by adding a largely excessive amount of 0.1% formic acid 50% CH$_2$CN aqueous solution thereto, stirring the resultant, and allowing the resultant solution to pass through RP-HPLC (FIG. 10). Thirty minutes after the convergence of the reaction, an amide formation ratio was 87%. The amide formation ratio here was calculated based on an integrated value of an integrated intensity of the HPLC. ESI-MS: H-YGGFA-SH 9 m/z calcd. For C$_{25}$H$_{31}$N$_5$O$_6$S: [M+H]$^+$ 530.2, found for [M+H]$^+$ 530.2.

Figure 11:
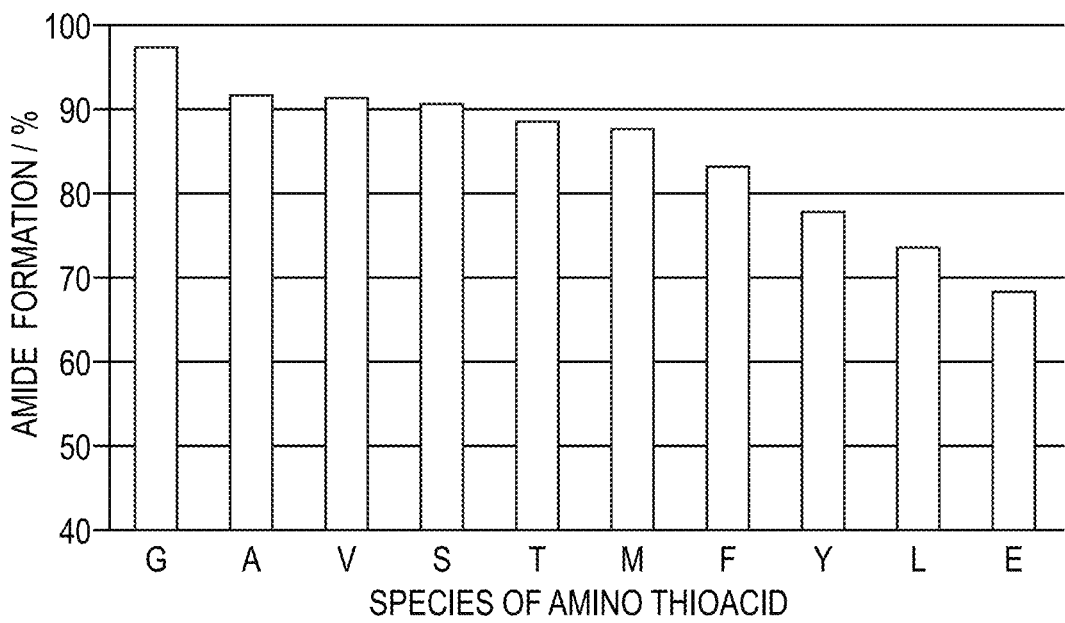
FIG. 11 illustrates amide formation ratios in accordance with species of amino thioacids. Abbreviations used in this drawing and amide formation ratios thereof are as follows: G=Gly-thioacid, 97%; A=Ala-thioacid, 92%; V=Val-thioacid, 91%; S=Ser-thioacid, 91%; T=Thr-thioacid, 89%; M=Met-thioacid, 88%; F=Phe-thioacid, 83%; Y=Tyr-thioacid, 78%; L=Leu-thioacid, 73%; and E=Gln-thioacid, 68%.

A similar reaction was performed with respect to the other amino thioacids, and amide formation ratios (%) obtained between peptide thioesters and amino thioacids thus obtained are all illustrated in FIG. 11.

Coupling of Peptide Thioester and H-Asn (diphenacyl-sialyloligosaccharide)-SH

[Formula 38]

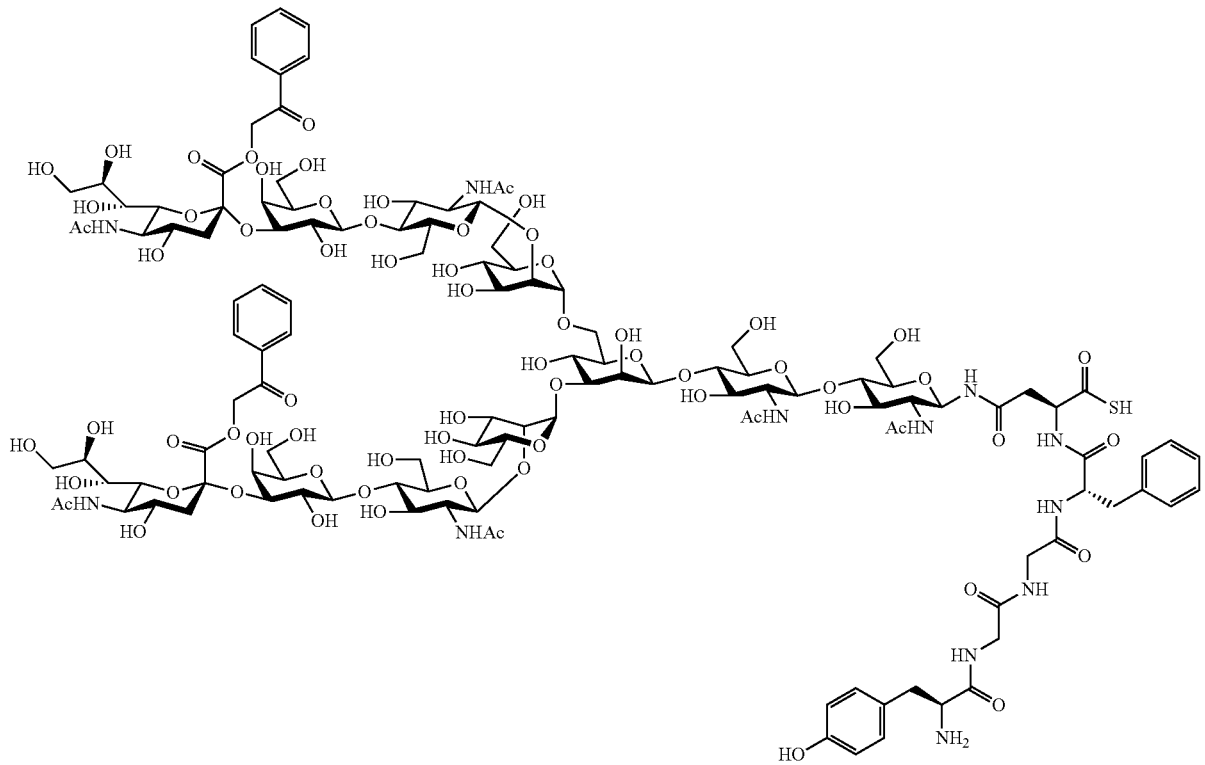

10

Figure 12:
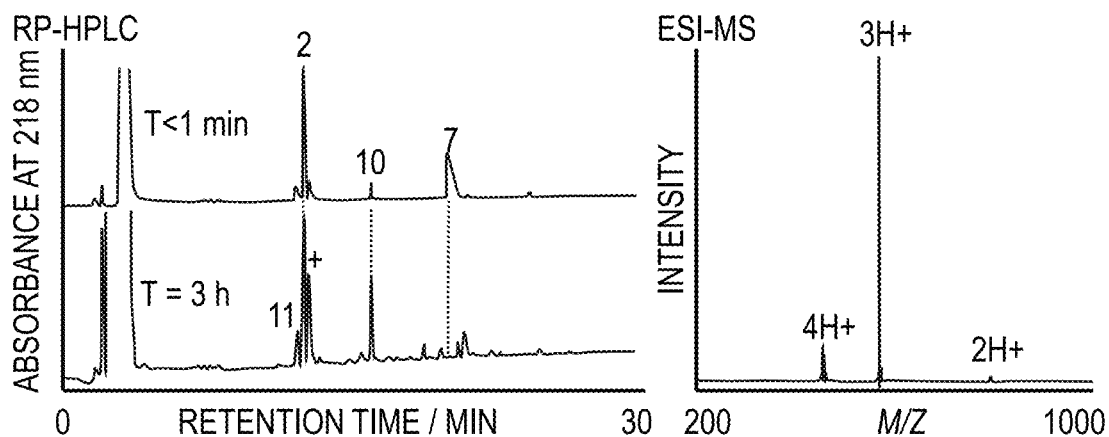
FIG. 12 illustrates an HPLC profile and an ESI-MS spectrum of a reaction product of thioanhydride ligation using an oligosaccharide: At t<0, a starting material, the peptide thioester 7, was present, and after performing coupling for 3 hours, a target product of H-YGGFN (sialyloligosaccharide)-SH 10 was synthesized. A reference sign 11 refers to oligosaccharide aspartamide, and a reference sign+ refers to H-YGGF-SH.

The peptide thioester 7 (0.060 mg, 0.10 μmol) was dissolved in 6.0 μL of DIEA (150 mM)-containing DMF under an Ar atmosphere. To the resultant reaction solution, synthesized H-Asn (diphenacyl-sialyloligosaccharide)-SH 2 (0.50 mg, 1.9 μmol) was added, and the resultant was reacted at room temperature. As a result of reaction tracking by HPLC, the reaction was found to converge after 3 hours of the reaction. An amide formation ratio in this condensation was found to be 46% (FIG. 12). The amide formation ratio here was calculated based on an integrated value of an integrated intensity of the HPLC. ESI-MS: m/z calcd. For $C_{126}H_{178}N_{12}O_{70}S$: $[M+2H]^{2+}$ 1508.5, $[M+3H]^{3+}$ 1005.9, $[M+4H]^{4+}$ 754.7, found for $[M+2H]^{2+}$ 1508.6, $[M+3H]^{3+}$ 1005.7, $[M+4H]^{4+}$ 754.8.

After completing the reaction, the resultant was immediately freeze dried, and the thus obtained peptide 10 was purified under the following conditions: HPLC (CAPCELL PAK C18 φ10×250 mm, 0.1% TFA aqueous solution: 0.1% TFACH₂CN solution=90:10 to 50:50, 50 minutes, flow rate: 3 mL/min).

Coupling of Peptide Thioester and H-Asn (asialo oligosaccharide)-SH

[Formula 39]

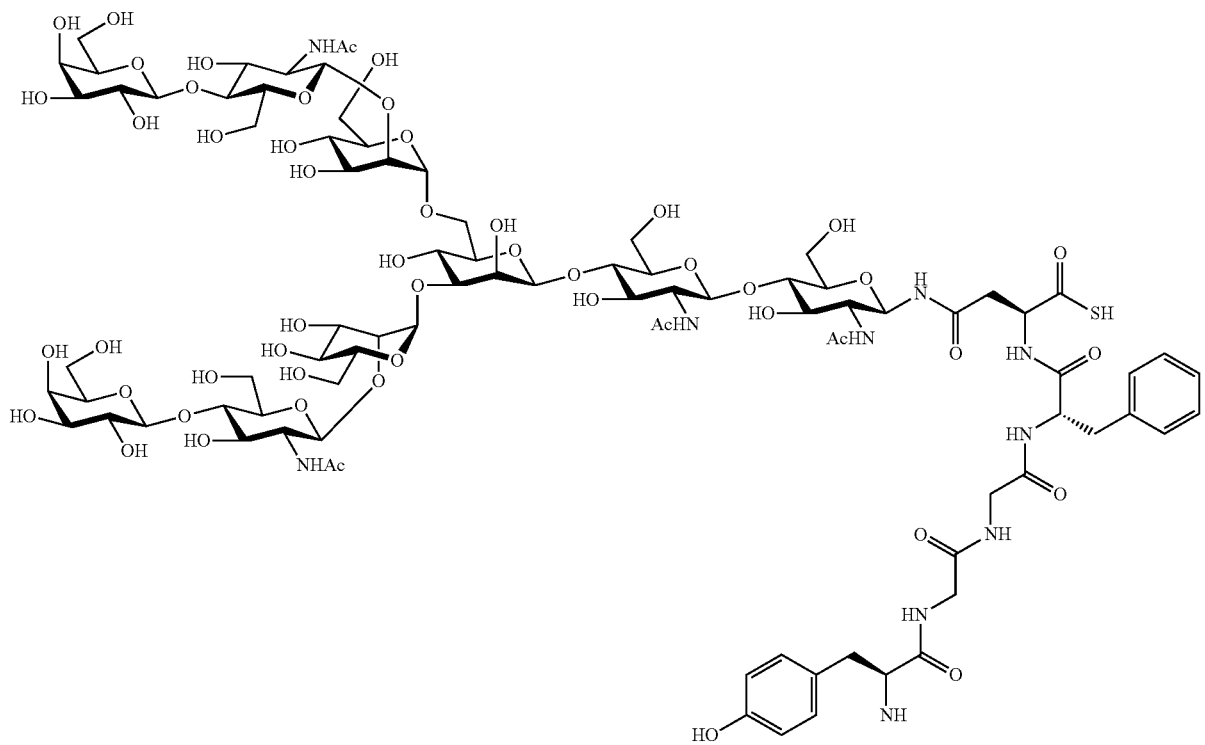

Figure 13:
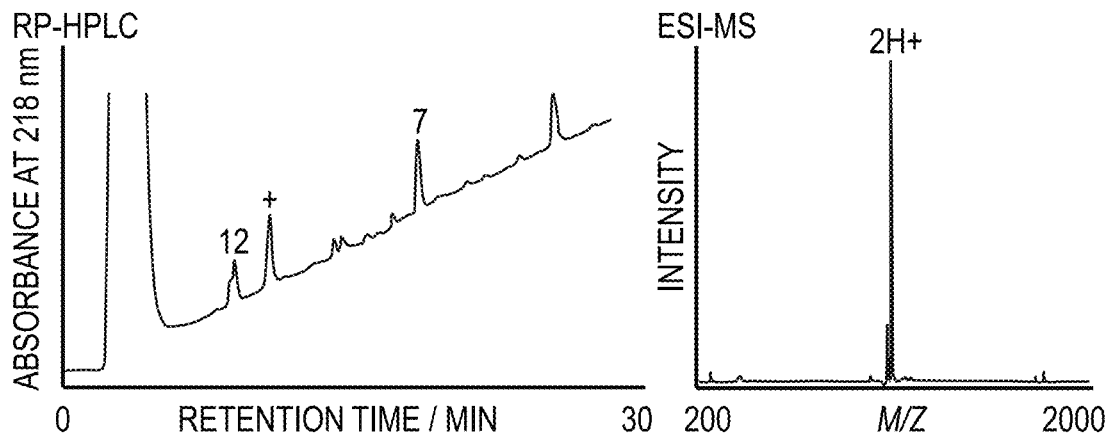
FIG. 13 illustrates an HPLC profile and an ESI-MS spectrum of a reaction product of thioanhydride ligation using an oligosaccharide. After performing coupling for 3 hours, a target product of H-YGGFN (asialo oligosaccharide)-SH 12 was synthesized. A reference sign+refers to H-YGGF-SH.

The peptide thioester 7 (0.15 mg, 0.017 μmol) was dissolved in 6.0 μL of DIEA (320 mM) —containing DMF under an Ar atmosphere. To the resultant reaction solution, synthesized H-Asn (asialo oligosaccharide)-SH 4 (0.01 mg, 0.082 μmol) was added, and the resultant was reacted at room temperature. As a result of reaction tracking by HPLC, the reaction was found to converge after 3 hours of the reaction. An amide formation ratio in this condensation was found to be 34% (FIG. 13). The amide formation ratio here was calculated based on an integrated value of an integrated intensity of the HPLC. ESI-MS: m/z calcd. For $C_{88}H_{134}N_{10}O_{52}S$: $[M+2H]^{2+}$ 1098.4, found for $[M+2H]^{2+}$ 1098.6.

Coupling of H-Tyr-Gly-Gly-Phe-Asn (diphenacyl-sialyloligosaccharide)-SH and H-Cys(Npys)-Gly-Tyr-Gly-OH Peptide This condensation reaction is a ligation reaction between a peptide thioacid and a peptide having an N-terminal Npys-modified. This reaction was performed referring to a method of Tam et al. (Liu, C.; Rao, C.; Tam, J. P., Acyl Disulfide-Mediated Intramolecular Acylation for Orthogonal Coupling Between Unprotected Peptide Segments, Mechanism and Application, Tetrahedron Letters, 1996, 37, 933-936).

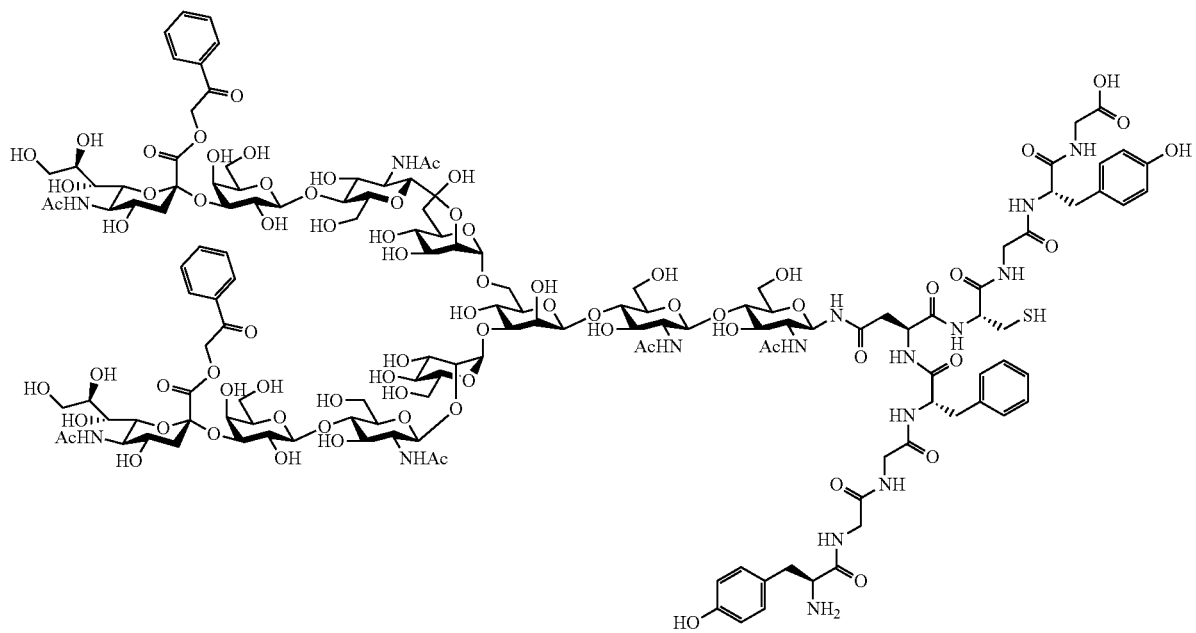

[Formula 40]

Figure 14:
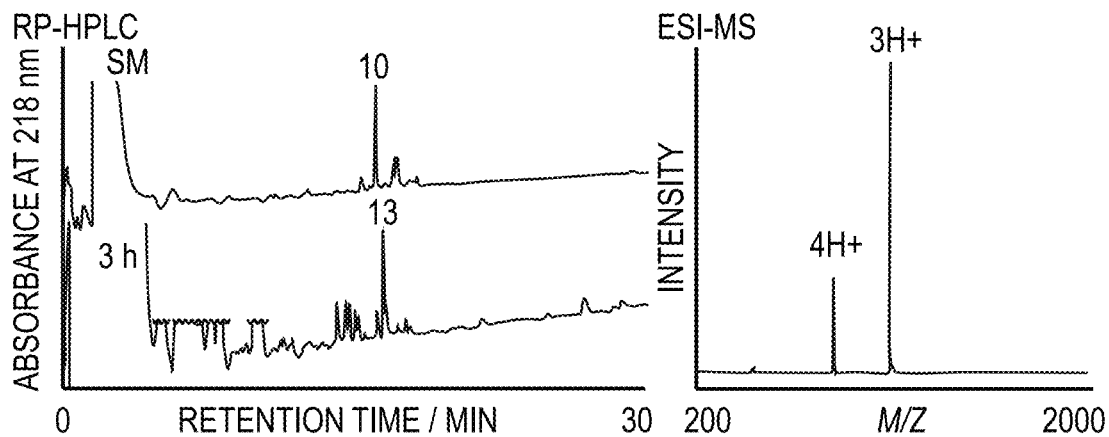
FIG. 14 illustrates an HPLC profile of a coupling product of an oligopeptide 10 and a peptide 8. After performing coupling for 3 hours, a target product of H-YGGFN (sialyloligosaccharide) CGYG-OH 13 was synthesized.

The obtained peptide 10 (0.29 mg, 0.096 μmol) was dissolved in 19.0 μL of DMF, and Npys-modified peptide 8 (0.1 mg, 0.18 μmol) was further added thereto. After performing the reaction for 2.5 hours, dithiothreitol was added to the resultant solution to converge the reaction. The reaction was checked by HPLC to confirm that ligation had been quantitatively performed (FIG. 14). ESI-MS: m/z calcd. For $C_{142}H_{200}N_{16}O_{76}S$: $[M+3H]^{3+}$ 1127.4, $[M+4H]^{4+}$ 845.8, found for $[M+2H]^{2+}$ 1127.1, $[M+3H]^{3+}$ 845.6.

[Example 2] Synthesis of Glycopeptide Using Auxiliary Group (1) Ligation on N-Terminal Side of Sugar Chain (1-1) Synthesis of Auxiliary Group An auxiliary group represented by a chemical formula, $C_{23}H_{22}OS$, was synthesized in accordance with the following reaction scheme:

[Formula 41]

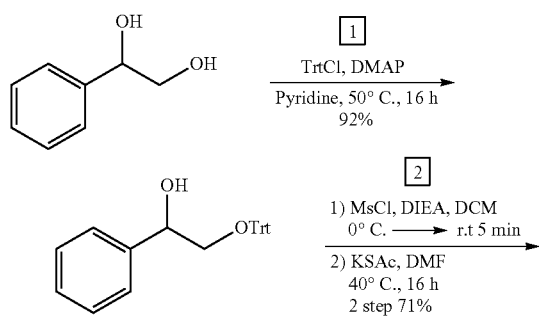

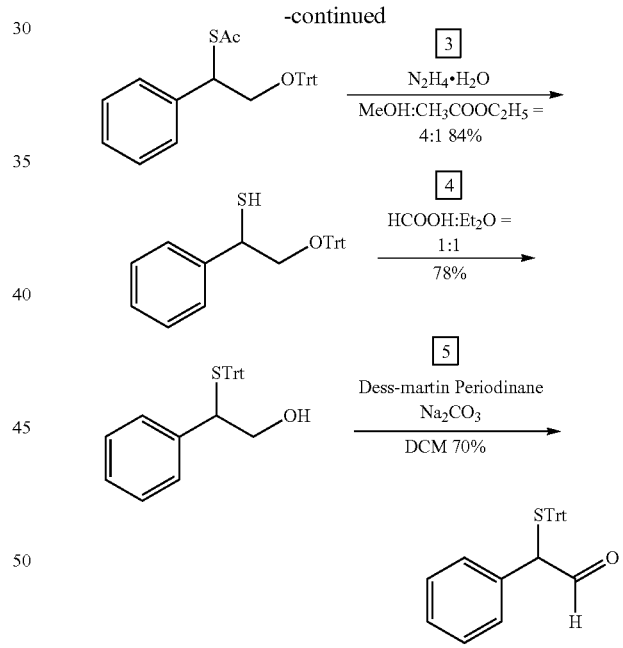

Reaction 1

An eggplant flask was charged with 1-phenylethane-1,2-diol (3.96 g, 28.9 mmol), TrtCl (8.77 g, 31.8 mmol, 1.1 equivalents), DMAP (0.354 g, 2.89 mmol, 0.1 equivalents), and a stir bar, and the resultant was dried in a vacuum line for 1 hour. After the atmosphere was replaced with argon, pyridine (72 ml, 400 mM) was added thereto, followed by stirring overnight in an oil bath at 50° C. During this, reaction tracking was performed by TLC (eluent: hexane: ethyl acetate=2:1). After 16 hours, the resultant was concentrated under reduced pressure using a vacuum pump to remove pyridine. After sufficiently removing pyridine, the resultant was diluted with ethyl acetate, and extracted with a saturated ammonium chloride aqueous solution, a saturated saline solution, and H$_2$O. The organic layer was concentrated under reduced pressure, and purified using a silica gel column (diameter: 30 mm, eluent: hexane:ethyl acetate=11:1) to obtain a target product (10.1 g, 92%).

Chemical Formula: C$_{27}$H$_{24}$O$_2$
[M+Na]$^+$: Cal.403.8 Found. 403.3
[M+K]$^+$: Cal.419.8 Found. 419.3
$^1$H NMR (CDCl$_3$, 400 MHz)
δ: 7.42-7.23 (m, 20H), 4.76 (m, 1H), 3.45 (m, 1H), 3.28 (m, 1H), 2.76 (d, 1H)

Reaction 2

1-Phenyl-2-(trityloxy)ethanol (7.11 g, 18.7 mmol) was dissolved in DCM (95 mL, 200 mM), DIEA (6.5 mL, 37.4 mmol, 2 equivalents) was added thereto in an ice bath, and then, MsCl (1.75 mL, 22.4 mmol, 1.2 equivalents) was added thereto slowly in a dropwise manner. After completing the dropwise addition, the ice bath was removed, and the temperature was gradually restored to room temperature. During this, reaction tracking was performed by TLC (eluent: hexane:ethyl acetate=4:1). After 5 minutes, the resultant was extracted with a saturated ammonium chloride aqueous solution, a saturated saline solution, and H$_2$O. MgSO$_4$ was added to the organic layer for filtration, and the resultant was concentrated under reduced pressure, and dried in a vacuum line for 1 hour. The resultant in a crude form was dissolved in DMF (250 mL, 150 mM), KsAc (4.27 g, 37.4 mmol, 2 equivalents) was added thereto, and the resultant was stirred overnight in an oil bath at 40° C. During this, reaction tracking was performed by TLC (eluent: hexane:ethyl acetate=4:1). The resultant was diluted with ethyl acetate, and extracted with a saturated saline water. The resultant was concentrated under reduced pressure, and purified using a silica gel column (diameter: 50 mm, eluent: hexane:toluene=1:1) to obtain a target product (5.82 g, 71%).

Chemical Formula: C$_{29}$H$_{26}$O$_2$S
[M+Na]$^+$: Cal. 461.0 Found. 461.3
[M+K]$^+$: Cal. 477.2 Found. 477.5
$^1$H NMR (CDCl$_3$, 400 MHz)
δ: 7.35-7.21 (m, 20H), 4.85 (t, 1H), 3.45 (d, 1H), 3.41 (d, 1H), 2.30 (S, 3H)

Reaction 3

S-(1-Phenyl-2-(trityloxy)ethyl)ethanethioate (5.19 g, 11.9 mmol) was dissolved in methanol: ethyl acetate=4.1 (118 mL, 100 mM), and N$_2$H$_4$—H$_2$O (0.865 mL, 17.9 mmol, 1.5 equivalents) was slowly added thereto in a dropwise manner, followed by stirring at room temperature. During this, reaction tracking was performed by TLC (eluent: hexane:toluene=3:1). After 1 hour, the resultant was diluted with ethyl acetate, and extracted with a saturated ammonium chloride aqueous solution, a saturated saline solution, and H$_2$O. The organic layer was concentrated under reduced pressure, and purified using a silica gel column (diameter: 50 mm, eluent: hexane:toluene=3:1) to obtain a target product (3.98 g, 84%).

Chemical Formula: C$_{27}$H$_{24}$OS
[M+Na]$^+$: Cal. 419.5 Found. 419.4
[M+K]$^+$: Cal. 435.2 Found. 435.1
$^1$H NMR (CDCl$_3$, 400 MHz)
δ: 7.40-7.20 (m, 20H), 4.09 (q, 1H), 3.45 (m, 2H), 2.33 (S, 1H)

Reaction 4

1-Phenyl-2-(trityloxy)ethane-1-thiol (3.58 g, 9.03 mmol) was dissolved in formic acid:Et$_2$O=1:1 (30 mL, 300 mM), followed by stirring at room temperature. During this, reaction tracking was performed by TLC (eluent: hexane:ethyl acetate=6:1). Immediately after this, piperidine (about 20 mL) was slowly added thereto in an ice bath for quenching, and the resultant reaction solution was diluted with ethyl acetate, and extracted with a saturated sodium carbonate aqueous solution, a saturated saline solution, and H$_2$O. The organic layer was concentrated under reduced pressure, and purified using a silica gel column (diameter: 50 mm, eluent: hexane:ethyl acetate=6:1) to obtain a target product (2.80 g, 78%).

Chemical Formula: C$_{27}$H$_{24}$OS
[M+Na]$^+$: Cal. 419.5 Found. 419.3
[M+K]$^+$: Cal. 435.2 Found. 435.0
$^1$H NMR (CDCl$_3$, 400 MHz)
δ: 7.44-7.23 (m), 3.46 (m, 1H), 3.38 (t, 1H), 3.31 (m, 1H), 1.50 (t, 1H)

Reaction 5

Na$_2$CO$_3$ (about 6 equivalents) was added to 2-phenyl-2-(tritylthio)ethanol (1.9 g, 4.91 mmol), and the resultant was dissolved in 50 mL of DCM. To the resultant, Dess-Martin periodinane (DMP) (2.29 g, 5.40 mmol, 1.1 equivalents) dissolved in 48 mL of DCM was added in small aliquots in a dropwise manner. The reaction was completed in 10 minutes, and during this, reaction tracking was performed by TLC (eluent: hexane:DCM=1:3). The resultant was diluted with an excessive amount of Et$_2$O, and extracted with a saturated sodium carbonate aqueous solution, a saturated saline solution, and H$_2$O. At this point, a white polymer-like substance was formed between the aqueous layer and the organic layer, but when the extraction operation was continued, most of the substance moved to the aqueous layer. Thereafter, the resultant was concentrated under reduced pressure within a draft, and purified using a silica gel column (hexane:DCM=1:3, diameter: 30 mm) to obtain a target product (1.35 g, 70%).

Chemical Formula: C$_{27}$H$_{22}$OS
[M+Na]$^+$: Cal. 417.1 Found. 417.2
[M+K]$^+$: Cal. 433.2 Found. 433.3
1H NMR (CDCl$_3$, 400 MHz)
δ: 8.99 (d, 1H) 7.44-7.21 (20H, m), 3.99 (d, 1H)

(1-2) Introduction of Auxiliary Group into Serine

The auxiliary group synthesized as described above was introduced into a serine in accordance with the following reaction scheme:

[Formula 42]

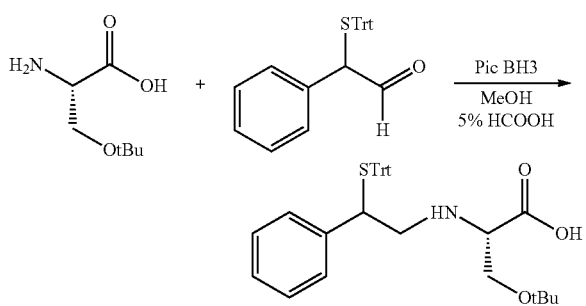

2-Phenyl-2-(tritylthio)acetaldehyde (173.5 mg, 0.438 mmol, 1.1 equivalents) was dissolved in methanol, and to the resultant, 0-(tert-butyl)-L-serine (64.2 mg, 0.398 mmol), borane-2-picoline complex (85.2 g, 0.796 mmol, 2 equivalents), and formic acid were added in the stated order. During this, reaction tracking was performed by TLC (eluent: ethyl acetate:methanol=1:1). After 5 hours, the resultant was diluted with ethyl acetate, and extracted with a saturated sodium carbonate aqueous solution, a saturated saline solution, and H₂O. The organic layer was concentrated under reduced pressure, and purified using a silica gel column (hexane:ethyl acetate=4:1, diameter: 15 mm) to obtain a target product (96.1 mg, 45%).

Chemical Formula: $C_{34}H_{37}NO_3S$ $[M+H]^+$: Calcd. 540.25 Found 540.1

(1-3) Introduction of Auxiliary Group into Glycosylated Amino Acid

The auxiliary group was introduced into a disialo glycosylated amino acid in accordance with the following reaction scheme:

[Formula 43]

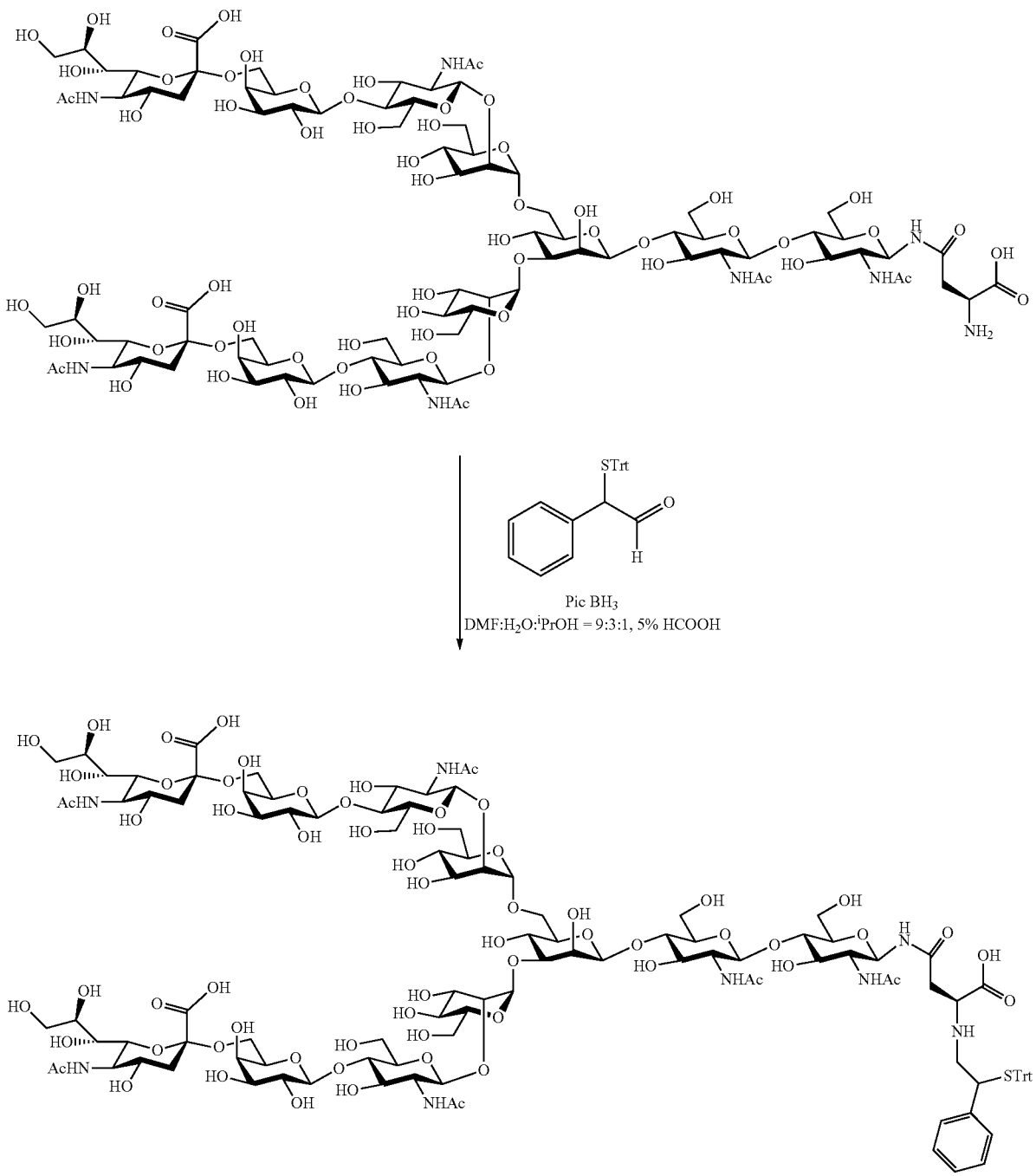

Figure 15:
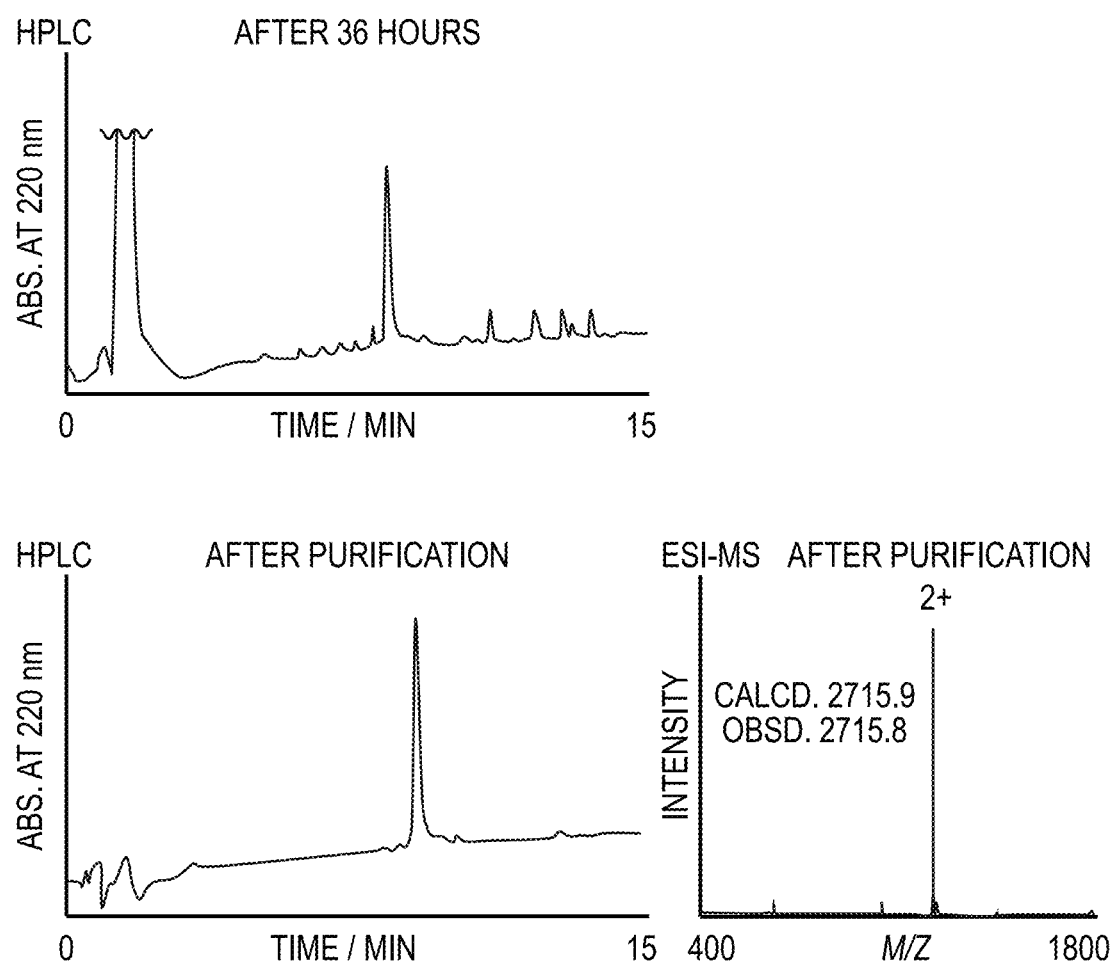
FIG. 15 illustrates an HPLC profile and an ESI-MS spectrum of a reaction product obtained after a reaction of introducing an auxiliary group into a disialo sugar chain.

Emoc-Asn (sialyl oligosaccharide) (51.4 mg, 21.4 μmol) dissolved in H₂O (0.6 mL) and 2-phenyl-2-(tritylthio) acetaldehyde (123.6 mg, 0.321 mmol, 15 equivalents) dissolved in DMF (1.8 mL) and isopropanol (0.2 mL) were mixed, and formic acid was added thereto to be a concentration of 5% (v/v). To the resultant solution, borane-2-picoline complex (36.1 mg, 0.321 mmol, 15 equivalents) was added, followed by stirring at 30° C. During this, reaction tracking was performed by TLC (eluent: 1 M ammonium acetate aqueous solution:isopropanol=2:3) and UPLC. After 36 hours, the resultant solution was concentrated under reduced pressure using a vacuum pump to remove DMF, and the resultant was purified by reverse phase HPLC to obtain a target product (34.6 mg, 59%, FIG. 15).

Chemical Formula: $C_{115}H_{166}N_8O_{64}S$ $[M+H]^+$: Cal. 2715.97 Found 2715.8

(1-4) Introduction of Protecting Group

A protecting group was introduced into sialic acid at a terminal of a glycosylated amino acid-auxiliary group complex in accordance with the following reaction scheme:

[Formula 44]

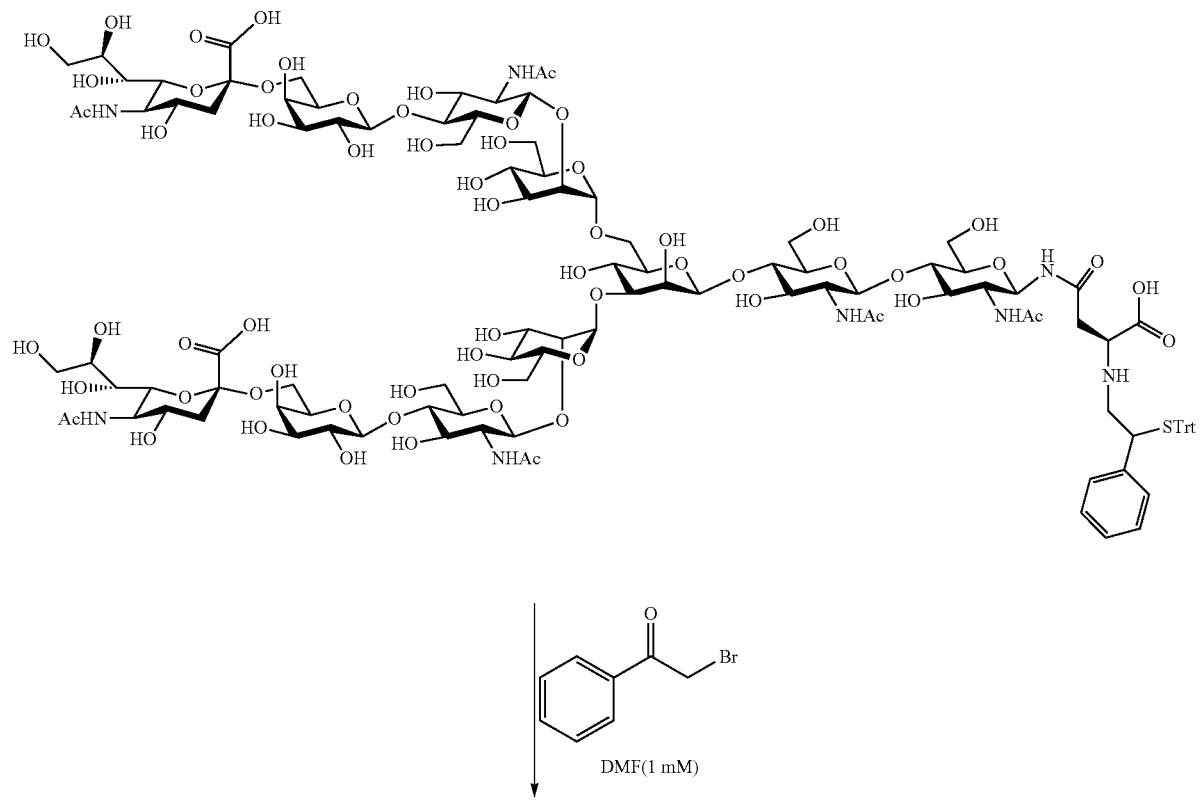

-continued

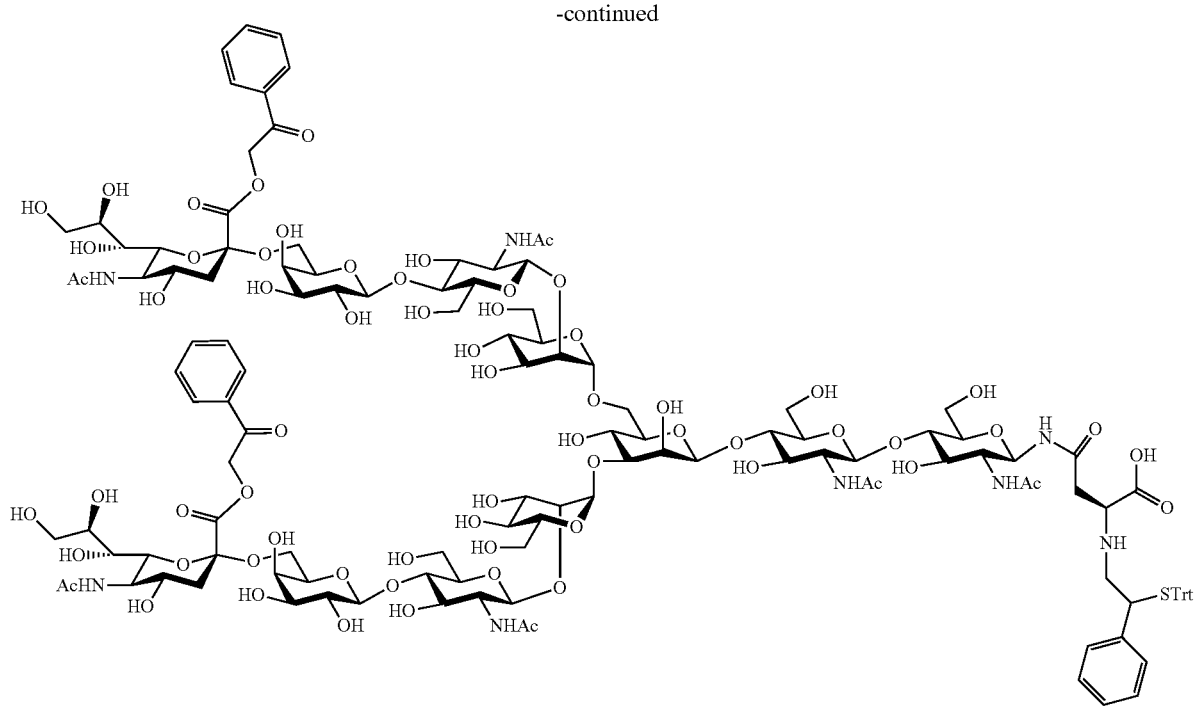

Figure 16:
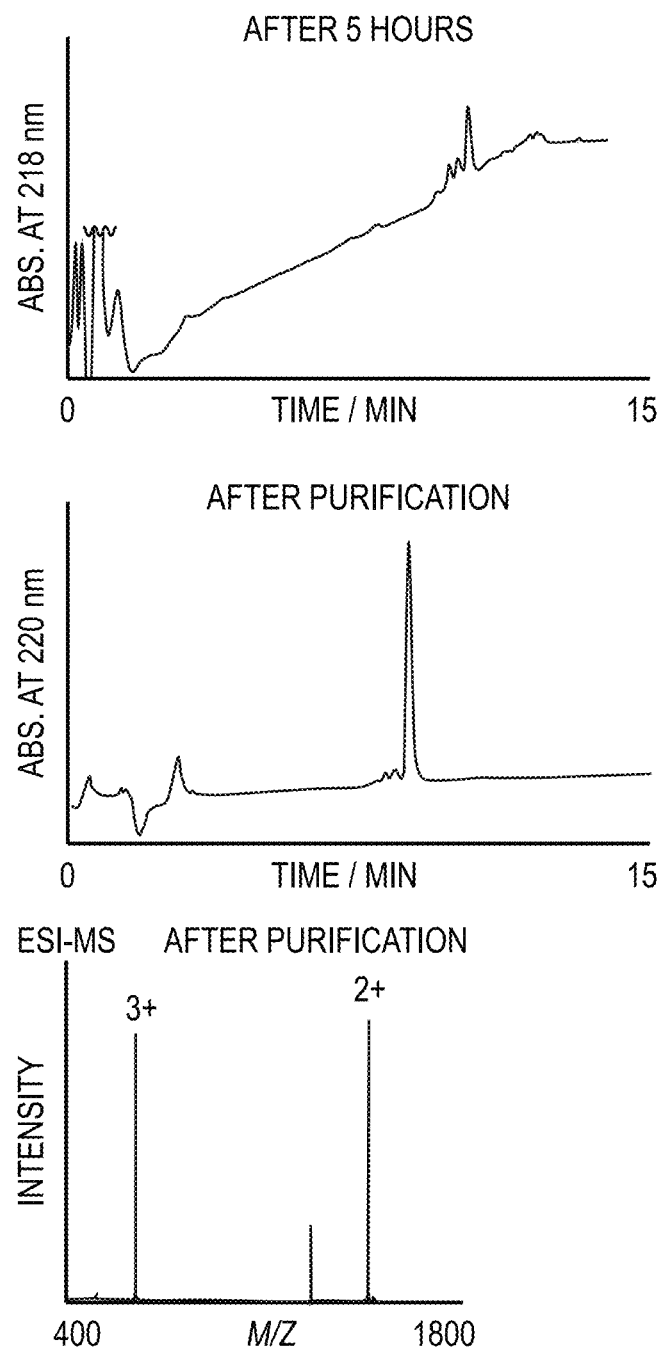
FIG. 16 illustrates an HPLC profile and an ESI-MS spectrum of a reaction product obtained after a reaction of introducing a protecting group into a disialo sugar chain-auxiliary group complex.

Aux-Asn (sialyl oligosaccharide) (10.6 mg, 3.68 mol) was allowed to pass through a cation exchange resin of Dowex50 and freeze dried. A solution obtained by dissolving the resultant in distilled water in a ratio of 500 μL per mg of sugar chain was adjusted to pH 4.0 using a 50 mg/mL cesium carbonate aqueous solution, and the resultant was freeze dried again. Thereafter, the resultant was dissolved in DMF (3.6 mL, 1 mM), and 2-bromo-1-phenylethane-1-one (3.62 mg, 18.4 mmol) was added thereto, followed by stirring at normal temperature for 5 hours. During this, reaction tracking was performed by UPLC, and the resultant was subjected to gel filtration with Sephadex G15 gel, and purified by reverse phase HPLC to obtain a target product (2.3 mg, 21%, FIG. 16).

Chemical Formula: $C_{131}H_{178}N_8O_{66}S$
$[M+N]^+$: Cal. 2951.94 Found 2952.0

(1-5) Ligation on N-Terminal Side Via Auxiliary Group

The glycosylated amino acid-auxiliary group complex obtained through the above-described procedures (1) to (4) was used in ligation to peptide thioester forms (LRLRGG-COSR and ALLX-COSR) in accordance with the following reaction scheme:

[Formula 45]

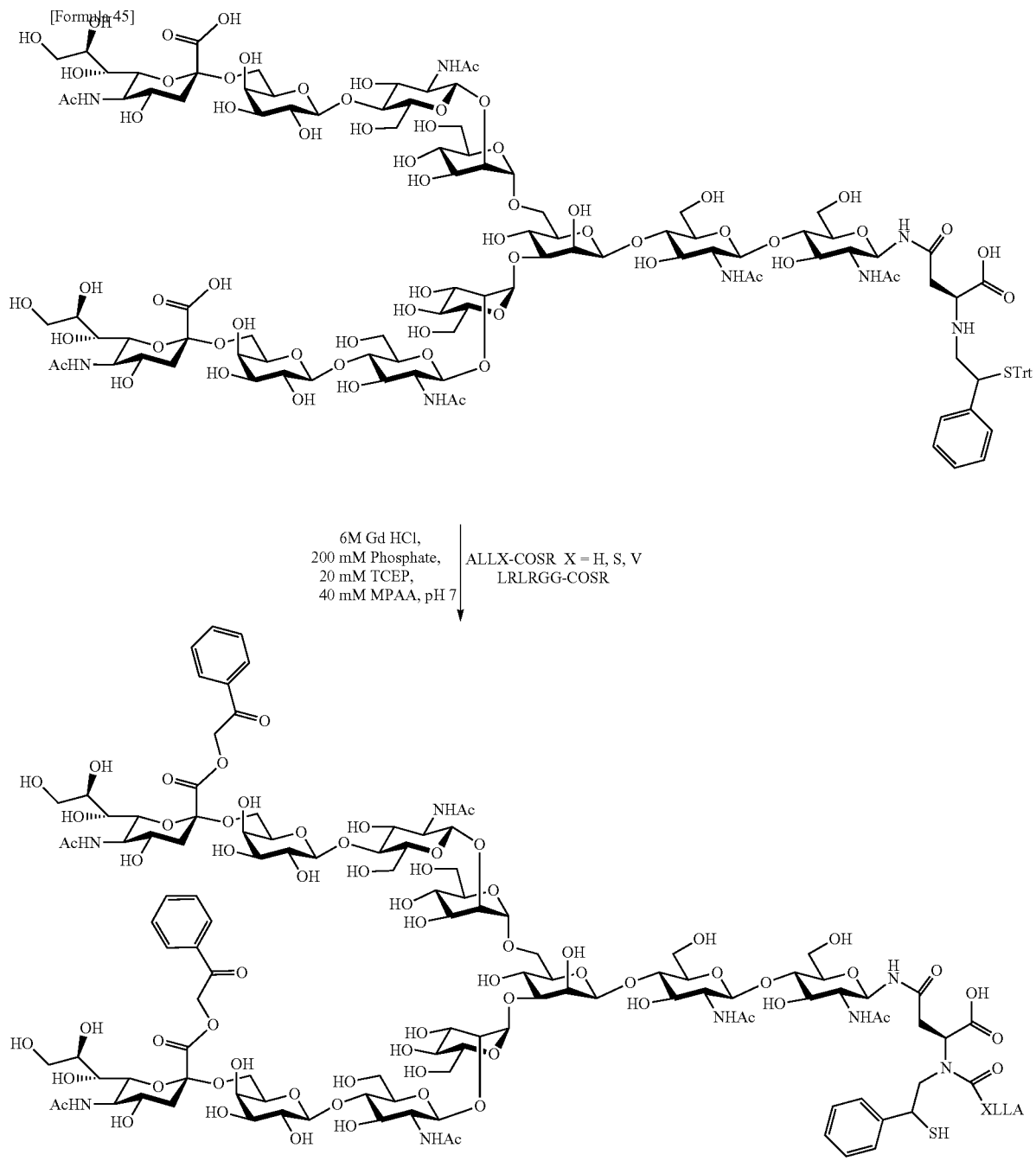

In either of the reactions, 50 μl each of buffers (6 M Gd·HCl, 200 mM phosphoric acid, 20 mM TCEP, and 40 mM MPAA) were used for dissolution to obtain a sugar chain-auxiliary group complex (Aux-Asn (diphenacyl-sialyloligosaccharide) (2.5 mM) and a peptide thioester form (5 mM), and to adjust the pH to 7. The resultant was allowed to stand still at normal temperature, and the reaction was tracked by UPLC.

LRLRGG

Figure 17:
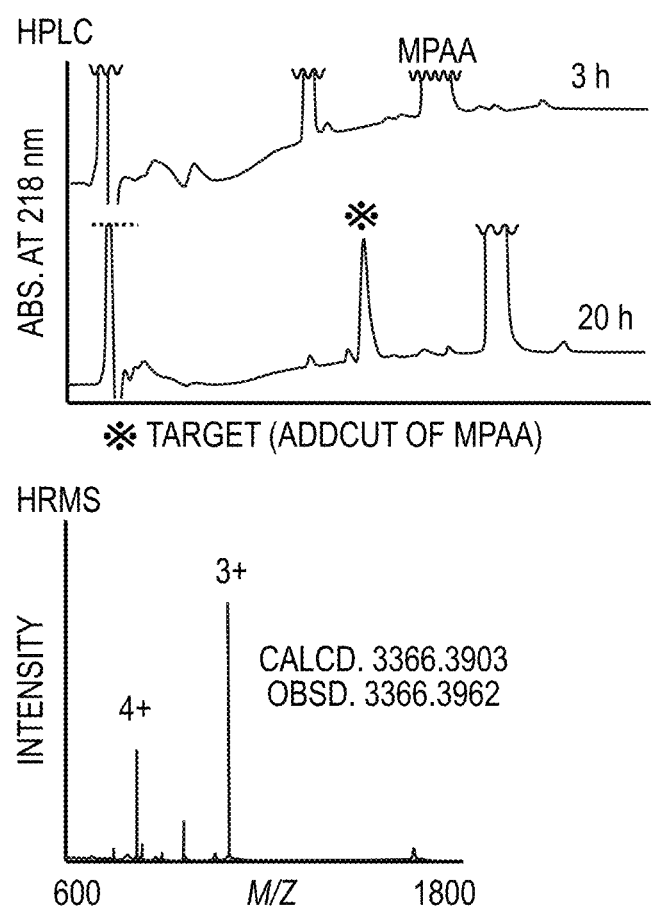
FIG. 17 illustrates an HPLC profile and an ESI-MS spectrum of a reaction product of ligation between a sugar chain-auxiliary group complex and a peptide thioester form (LRLRGG-COSR).

LRLRGG was obtained in the form of an MPAA adduct, but when TCEP was added, the whole was obtained in the form of a target ligation product (HPLC area yield >99%, FIG. 17).

Chemical Formula: $C_{140}H_{220}N_{20}O_{72}S$
$[M+H]^+$: Calcd. 3366.3903 Found 3366.3962

ALLH

Since a ligation product resulting from deprotection of a Pac group in a sugar chain was found, 200 mM MESNa and 0.5 μL of piperidine were added to the reaction system to deprotect all Pac groups, and then, an area yield was obtained (area yield: 88%, FIG. 18).

Chemical Formula: $C_{117}H_{186}N_{14}O_{68}S$
$[M+H]^+$: Calcd. 2908.13 Found 2908.2

ALLS

Since a ligation product resulting from deprotection of a Pac group in a sugar chain was found, an area yield was obtained including a deprotected form (area yield: 77%).

Chemical Formula: $C_{130}H_{196}N_{12}O_{71}S$ (ligation product having a Pac group not removed)

[M+H]$^+$: Calcd. 3094.18 Found 3094.32
ALLV

Since a ligation product resulting from deprotection of a Pac group in a sugar chain was found, an area yield was obtained including a deprotected form (area yield: 76%).

Chemical Formula: $C_{132}H_{200}N_{12}O_{70}S$
[M+H]$^+$: Calcd. 3106.22 Found 3106.38

(2) Ligation on N-Terminal Side of Sugar Chain (2-1) Synthesis of Sugar Chain Amino Acid NHNHBoc conversion of an amino acid (serine) C-terminal was performed in accordance with the following reaction scheme:

[Formula 46]

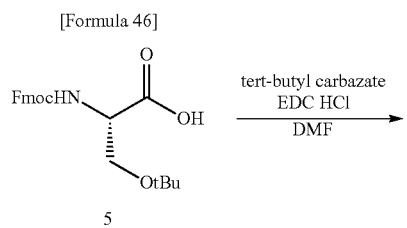

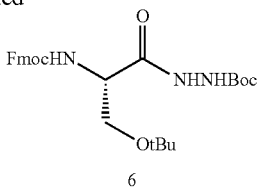

N-(((9H-Fluoren-9-yl)methoxy)carbonyl)-O-(tert-butyl)-L-serine (1.02 g, 2.61 mmol) was dissolved in DMF (12 mL, 217 mM), and tert-butyl carbazate (1.73 g, 13.0 mmol, 5 equivalents) and EDC·HCl (1.86 g, 9.70 mmol, 3.5 equivalents) were added thereto, followed by stirring at room temperature. During this, reaction tracking was performed by TLC (eluent: ethyl acetate or hexane:ethyl acetate=1:1). After 30 minutes, the resultant was diluted with ethyl acetate, and extracted with a saturated sodium carbonate aqueous solution and a saturated saline solution. The organic layer was concentrated under reduced pressure, and purified using a silica gel column (diameter: 30 mm, hexane: ethyl acetate=1:1) to obtain a target product (1.17 g, 90%).

Chemical Formula: $C_{27}H_{35}N_3O_6$
[M+Na]$^+$: Cal. 520.2 Found. 520.2
[M+K]$^+$: Cal. 536.3 Found. 536.3
$^1$H NMR (CDCl$_3$, 400 MHz)
δ: 7.65-7.25 (m, 10H), 5.70 (s, 1H), 4.40 (d, 2H), 4.32 (s, 3H), 3.81 (s, 1H), 1.26 (s, 9H)

Subsequently, a sugar chain was introduced in accordance with the following reaction scheme:

[Formula 47]

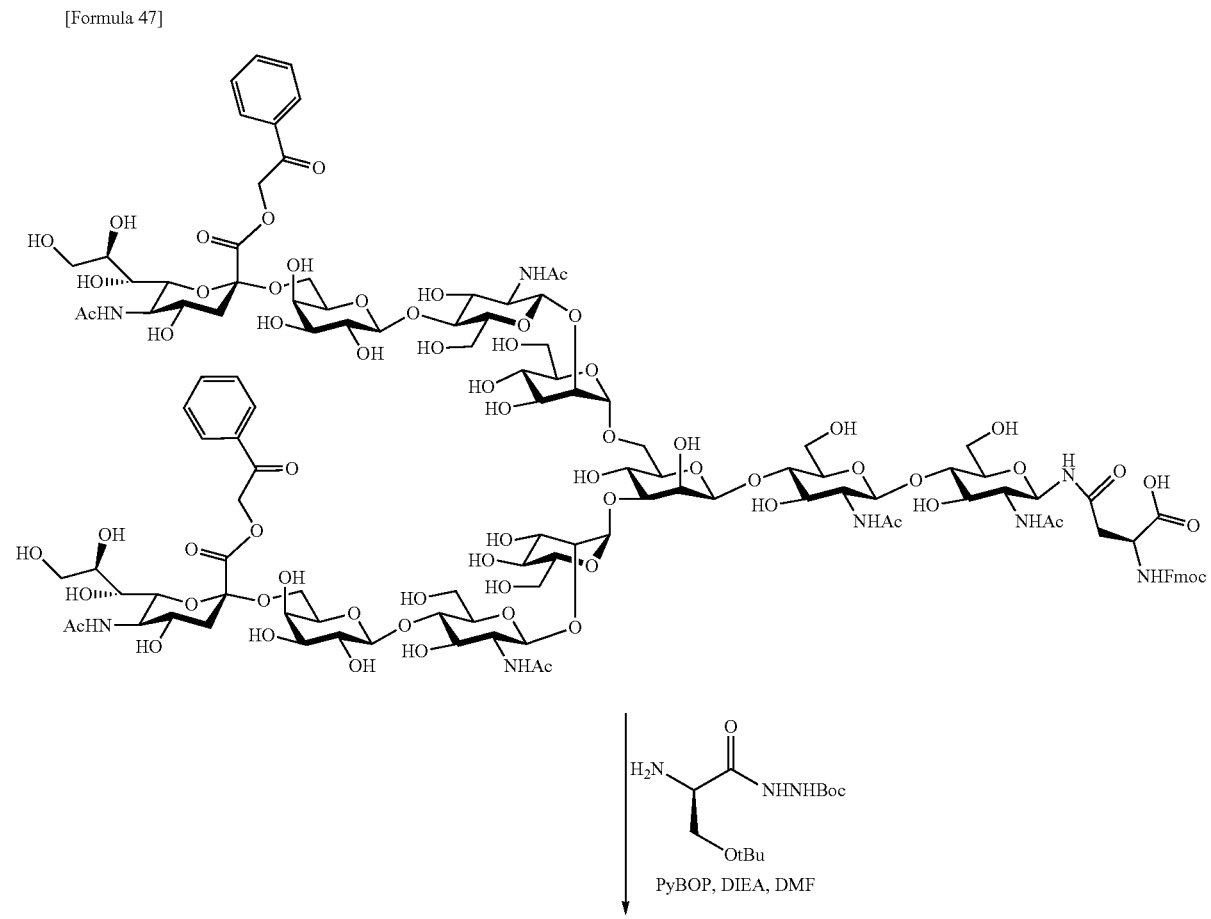

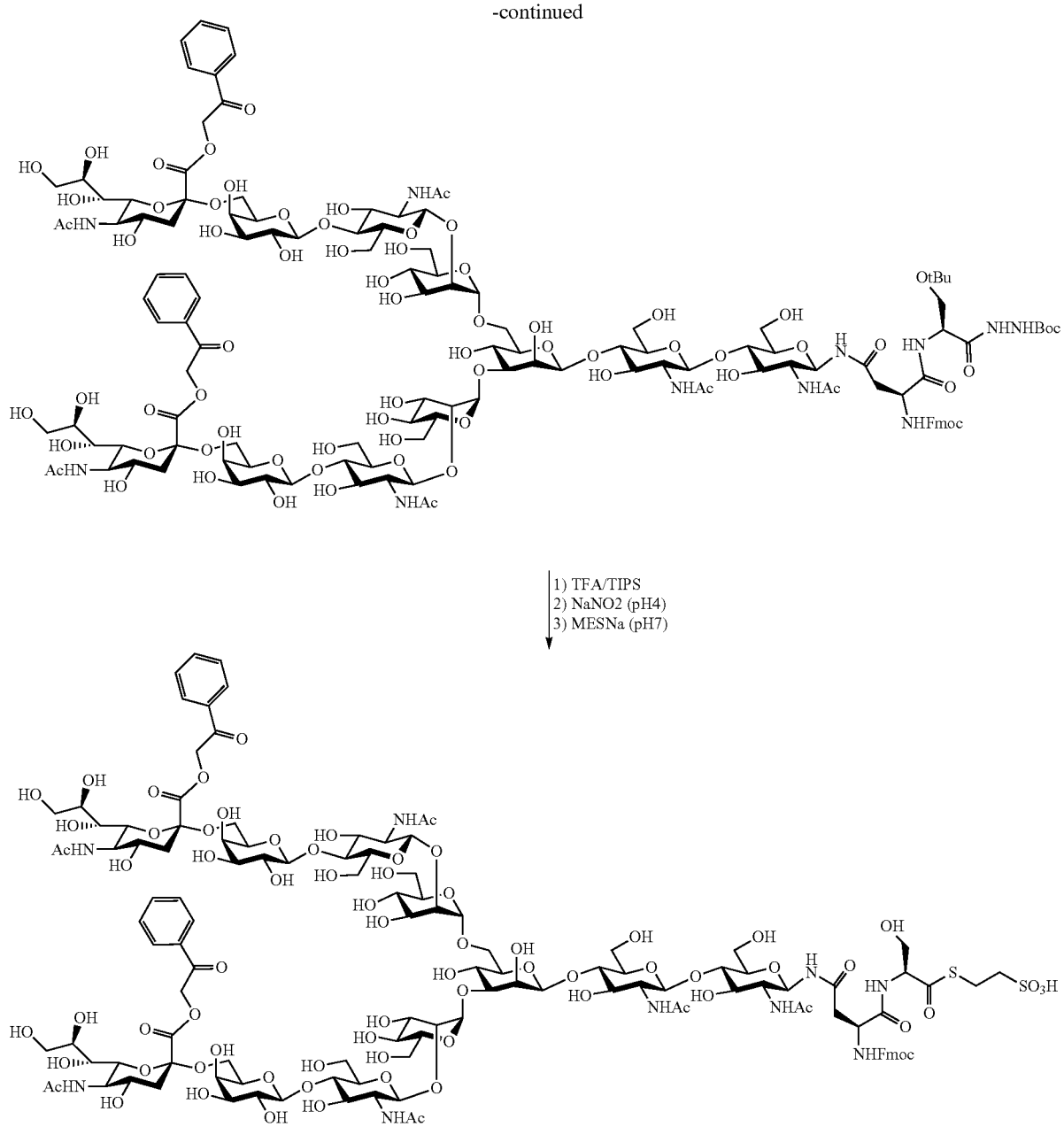

50

Amino Acid Condensation and Side Chain Deprotection

Figure 19:
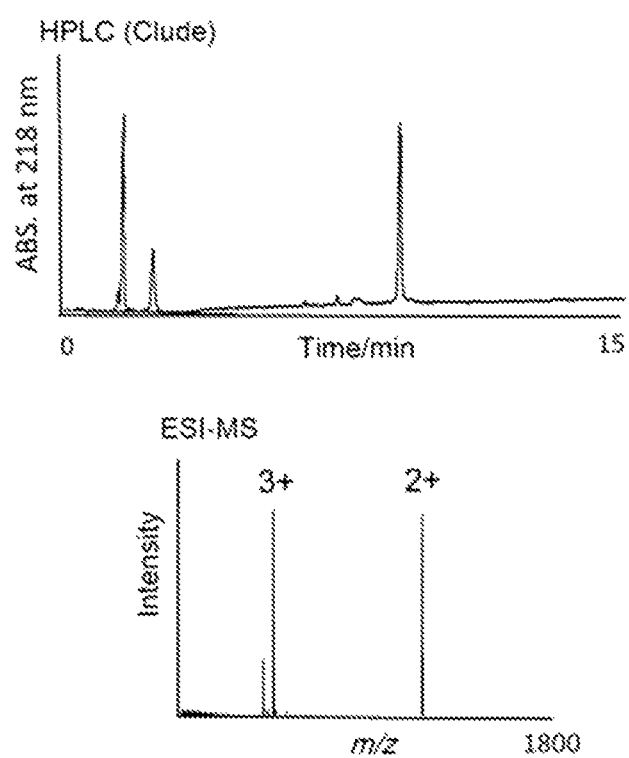
FIG. 19 illustrates an HPLC profile and an ESI-MS spectrum of a reaction product obtained after a condensation reaction of Fmoc-Asn (diphenacyl-sialyloligosaccharide and NH$_2$-Ser(OtBu)—NHNHBoc.

To Fmoc-Asn (diphenacyl-sialyloligosaccharide) (10.1 mg, 3.58 μmol), $NH_2$—Ser (OtBu)—NHNHBoc (4.9 mg, 17.9 mol, 5 equivalents) and PyBOP (9.5 mg, 17.9 μmol, 5 equivalents) dissolved in DMF (715 μL, 5 mM) were added. To the resultant, DIEA (4.2 μL, 25.1 μmol, 7 equivalents) was further added, followed by stirring at −20° C. for 20 minutes. During this, reaction tracking was performed by UPLC, and after completing the reaction, the reagent was removed by gel filtration with Sephadex LH-20, $CH_3CN$: $H_2O$=1:1, and the resultant was freeze dried (9.2 mg, 84%, FIG. 19). Next, TFA/TIPS (95:5, 200 μL) was added to the thus obtained sample, followed by stirring in an ice bath for 1 hour. Thereafter, cooled $Et_2O$ in a 10-fold amount was used to obtain a Boc, tBu deprotected form as a precipitate. Then, distilled water was added to the resultant for dilution, and the resultant was freeze dried (7.8 mg, 89%).

Preparation of Amino Acid C-Terminal

Figure 20:
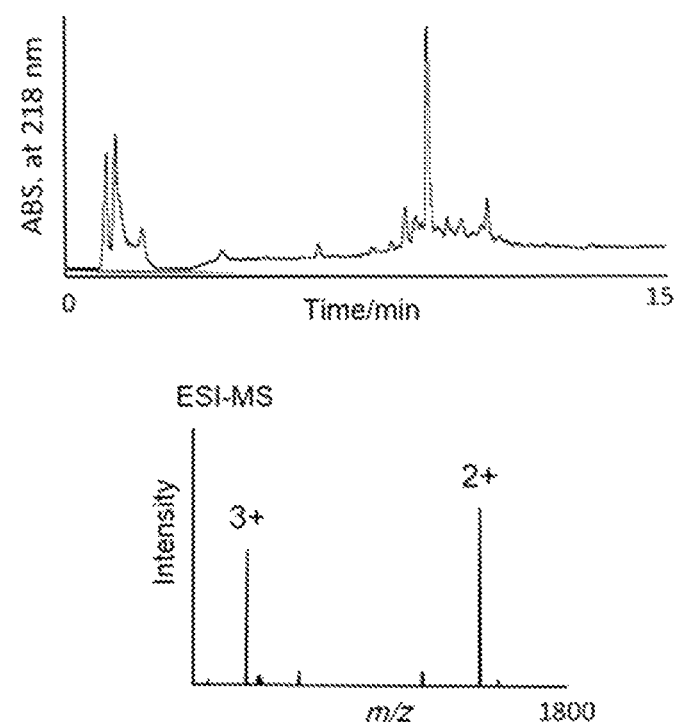
FIG. 20 illustrates an HPLC profile and an ESI-MS spectrum obtained after performing a reaction of converting an azide form at the C-terminal of a glycosylated amino acid (serine) to a thioester form.

Next, 50 μL of 10 mM $NaNO_2$ (6 M Gd·HCl, 200 mM phosphate buffer, pH 4.0) was added to the thus obtained sample, followed by stirring at −20° C. After 30 minutes, it was confirmed by UPLC that the terminal had been changed to an azide form, and then, MESNa was added to be a concentration of 200 mM in the sample to adjust the pH to 7. After 3 hours, it was confirmed by UPLC that the terminal had been changed to a thioester form, and then the sample was subjected to gel filtration (Sephadex LH-20, $CH_3CN$: $H_2O$=1:1) to obtain a target product (6.1 mg, 75%, FIG. 20).

Chemical Formula: $C_{124}H_{175}N_9O_{72}S_2$ $[M+H]^+$: Cal. 3007.98 Found 3007.84

(2-2) Ligation of Amino Acid on C-Terminal Side of Sugar Chain
A ligation reaction was performed on the C-terminal side of a sugar chain amino acid thioester form in accordance with the following reaction scheme:
[Formula 48]
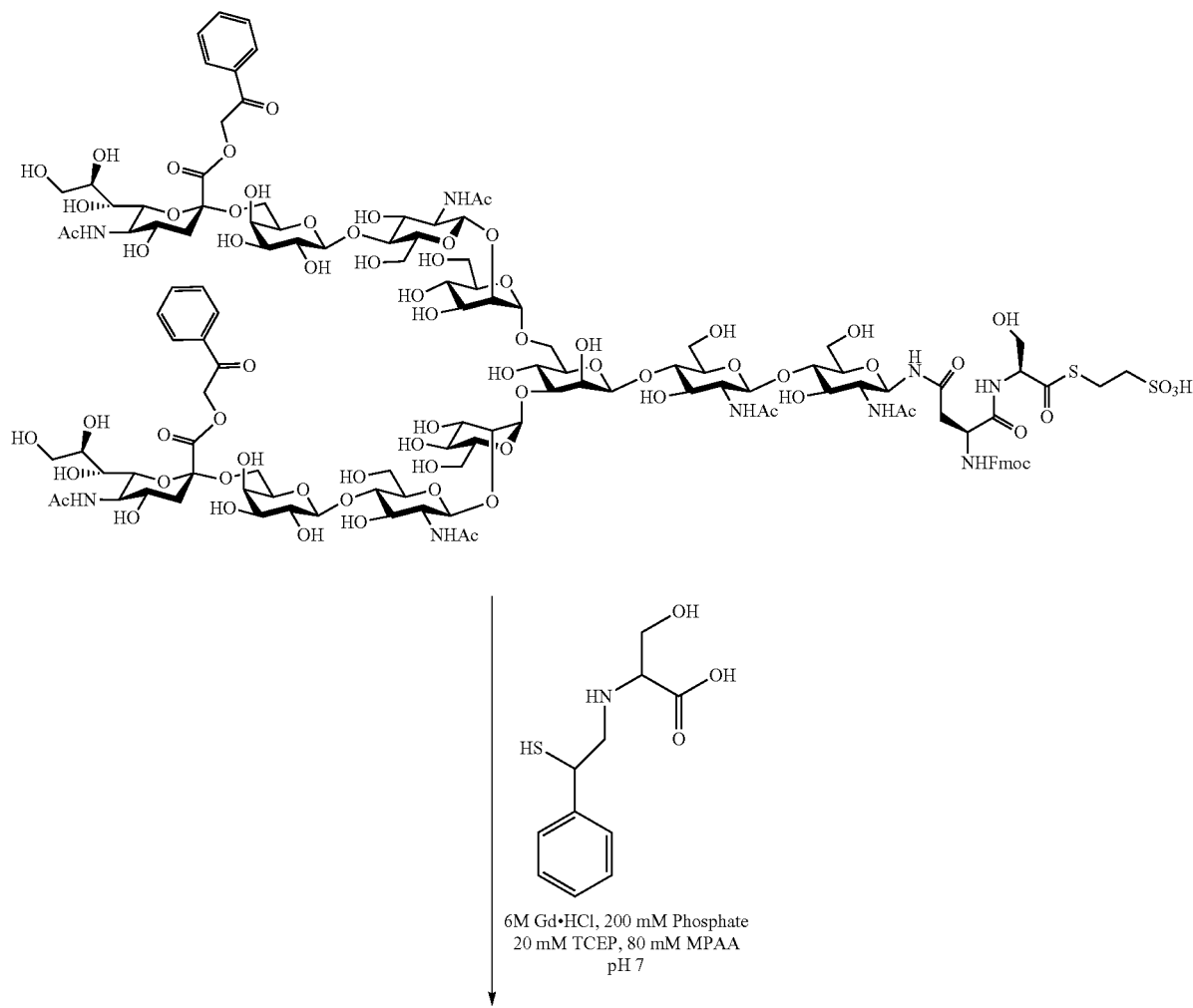

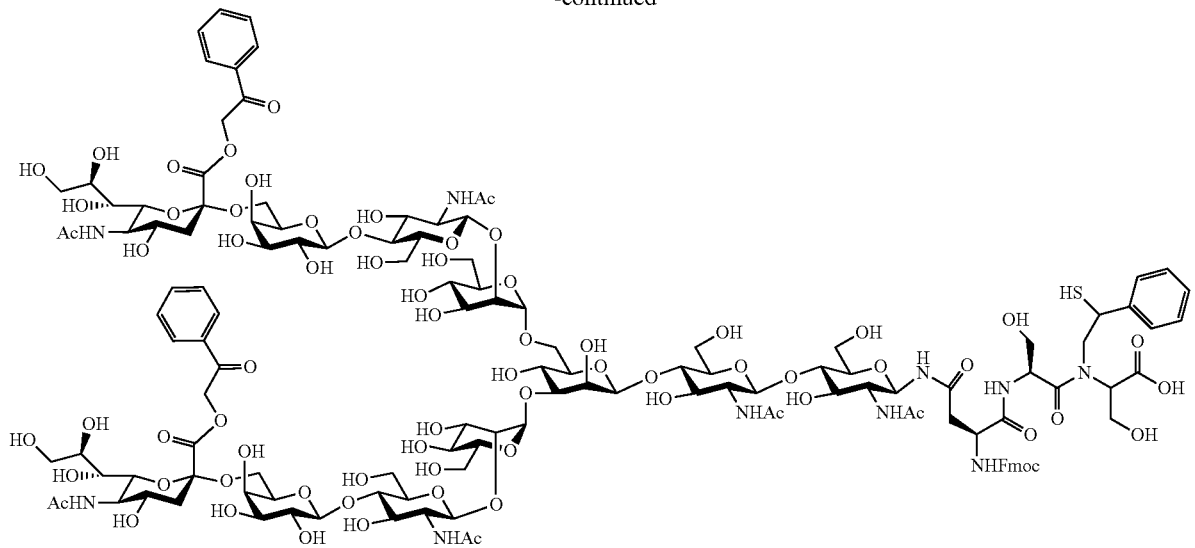

Fmoc-Asn (diphenacyl-sialyloligosaccharide)-Ser-COSR (0.4 mg, 0.13 μmol, 0.5 mM) and Aux (SH)-Ser-COOH (0.16 mg, 0.65 μmol, 5 mM) were dissolved in a buffer (GM Gd·HCl, 200 mM phosphoric acid, 20 mM TCEP, 80 mM MPAA), and the pH was adjusted to 7. The resultant was allowed to stand still at normal temperature, and reaction tracking was performed by UPLC. Raw material sugar chains all disappeared in 4 hours, and generation of a target product was confirmed by ESI-MS (FIG. 21).

Chemical Formula: $C_{133}H_{184}N_{10}O_{72}S$ $[M+H]^+$: Cal. 3106.99 Found 3107.01

[Example 3] Synthesis of Peptide Thioester (1) MENSa Thioesterification accompanying NS Transfer of C-Terminal CGC

[Formula 49]

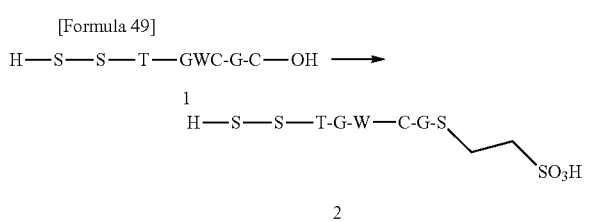

A 1.5 mL Eppendorf tube was charged with a peptide (H-SSTGWCGC-OH) 1 (1 equivalent, 0.50 mg, 0.6 μmol) and sodium 2-mercaptoethanesulfonate (MESNa, 10% (w/v), 31.3 mg, 0.19 mmol), and the resultant was dissolved in a 0.2 M citrate buffer solution containing 6M guanidine hydrochloride to adjust the pH to 3.5, and cause a reaction. The reaction was performed at 50° C. The reaction was tracked for 72 hours, and checked by LC/MS. The reaction was completed in 72 hours, cysteine released into the reaction solution was removed by Sep-Pak(R), and the resultant was freeze dried (result of mass spectrometry of a target product 2: M/Z 821.2). The target product 2 was subsequently used in a next reaction to perform synthesis of a compound having thioesterified tryptophan accompanying release of CysGly-thioester (FIG. 22).

(2) Terminal Thioesterification of C-Terminal CG-MESNa Thioester using MESNa

[Formula 50]

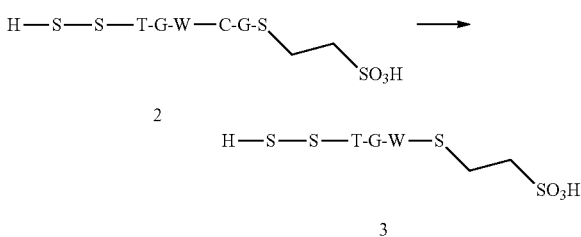

A 1.5 mL Eppendorf tube was charged with a peptide (H-SSTGWCG-MESNa) 2 (1 equivalent, 0.50 mg, 0.6 μmol) and sodium 2-mercaptoethanesulfonate (MESNa, 10% (w/v), 31.3 mg, 0.19 mmol), and the resultant was dissolved in a 0.2 M citrate buffer solution containing 6M guanidine hydrochloride to adjust the pH to 6.5, and cause a reaction. The reaction was performed at 50° C. The reaction was tracked for 8 hours, and checked by LC/MS. As a result, a peptide thioester 3 was obtained through release of CysGly-thioester (FIG. 23). A result of mass spectrometry of the target product 3: M/Z 661.1.

(3) Terminal Thioesterification of C-Terminal CG-MESNa Thioester Using MPAA

[Formula 51]

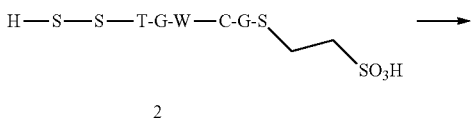

-continued

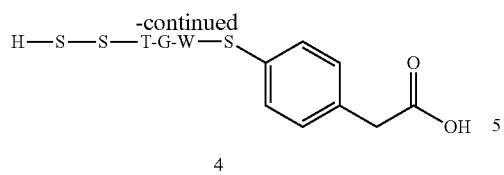

4

In the above-described reaction to obtain the peptide thioester 3, examination was made to obtain a thioester form 4 having mercaptophenylacetic acid (MPAA) added thereto by using MPAA having high leaving group ability. A 1.5 mL Eppendorf tube was charged with a peptide (H-SSTGWCG-MESNa) 2 (1 equivalent, 0.50 mg, 0.6 µmol) and mercaptophenylacetic acid 10% (w/v), 31.3 mg, 0.18 mmol), and the resultant was dissolved in a 0.2 M citrate buffer solution containing 6M guanidine hydrochloride to adjust the pH to 6.5, and cause a reaction to obtain the target product 4. The reaction was performed at 50° C. The reaction was tracked for 2 hours, and checked by LC/MS (FIG. 24). A result of mass spectrometry of the target product 4: M/Z 687.2.

(4) Introduction Reaction of Bis(2-Sulfanylethyl)Amino Group Accompanying NS Transfer of C-Terminal GC

[Formula 52]

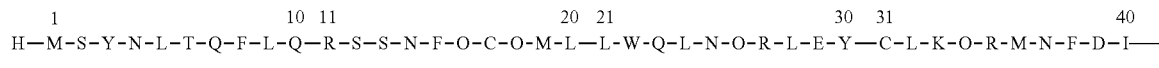

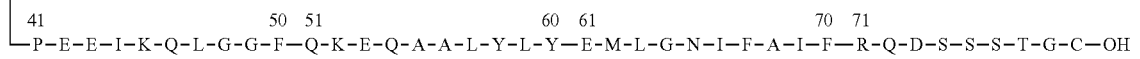

Seg1-Cys
Molecular Weight: 9391.78

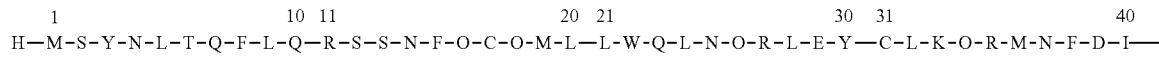

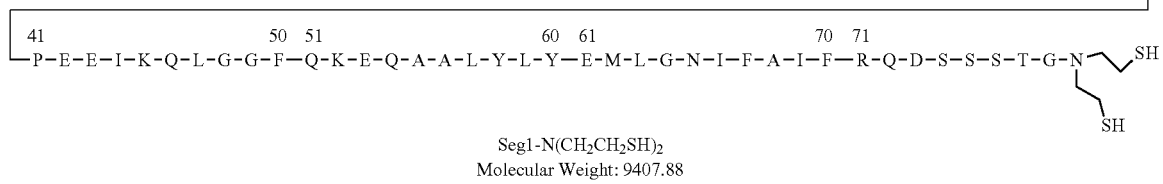

Seg1-N(CH$_2$CH$_2$SH)$_2$
Molecular Weight: 9407.88

Bis (2-sulfanylethyl) amine {HN(CH$_2$CH$_2$SH)$_2$·HCl (5% (w/v), 7.5 mg)} was added to a peptide (Seg 1) (1 equivalent, 0.50 mg), and the resultant was dissolved in a 0.2 M citrate buffer solution containing 6M guanidine hydrochloride to adjust the pH to 3.5, and cause a reaction. The reaction was performed at 50° C. The reaction was tracked for 50 hours, and checked by LC/MS (FIG. 25). A result of mass spectrometry of a target product, a peptide having a bis(2-sulfanylethyl)amino group at the C-terminal: [M+10H]$^{10+}$ 941.6955, [M+9H]$^{9-}$ 1046.2149, [M+8H]$^{8+}$ 1176.8641, [M+7H]$^{7+}$ 1344.8428, [M+6H]$^{6+}$ 1568.8149.

(5) Introduction of Bis(2-Sulfanylethyl)Amino Group Accompanying NS Transfer of C-Terminal

[Formula 53]

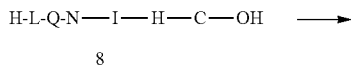

8

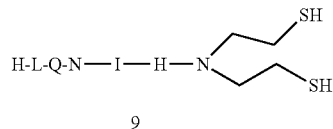

9

Figure 26:
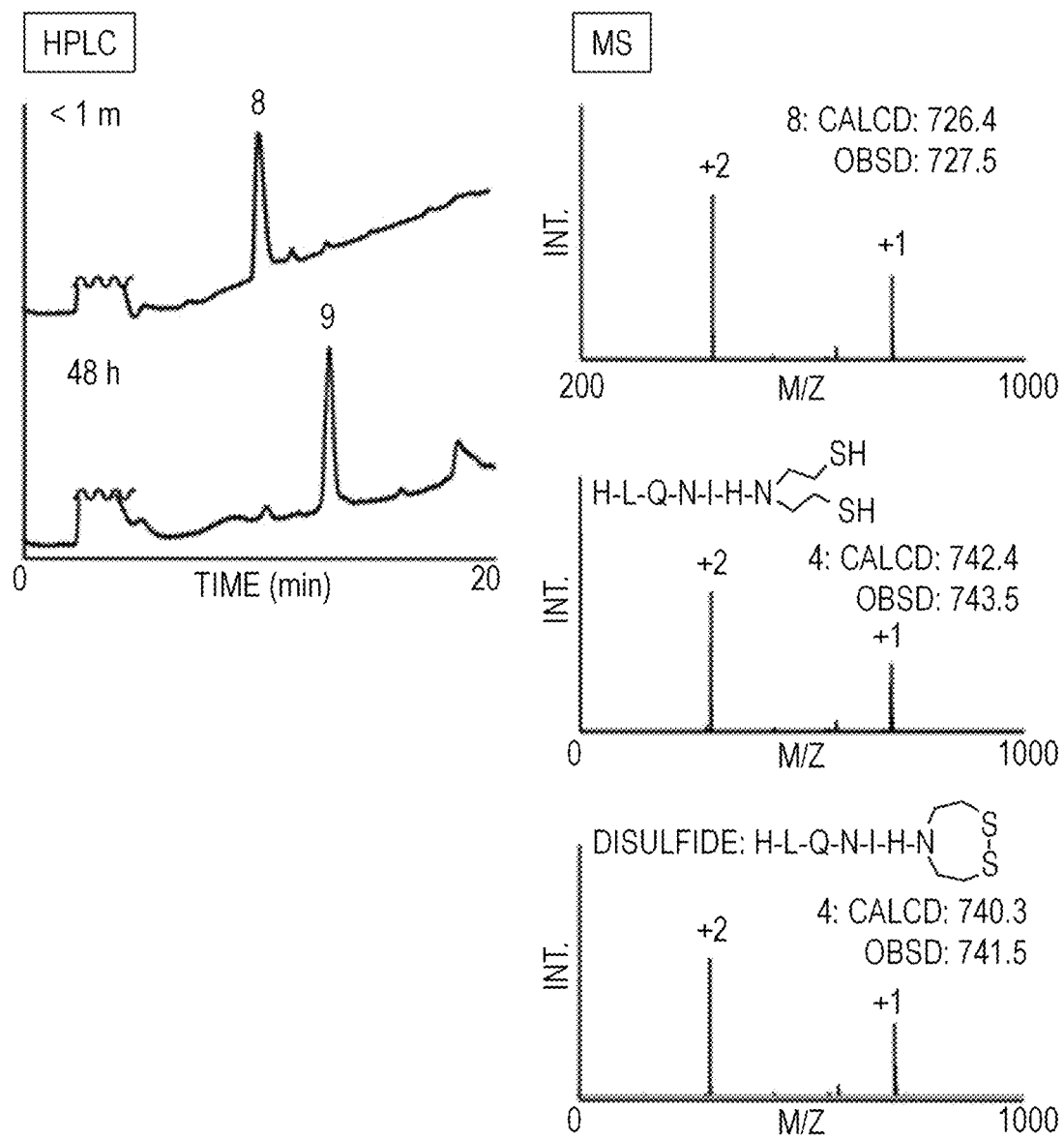
FIG. 26 illustrates LC/MS results obtained after a reaction between a peptide (H-LQNIHC-OH) 8 and bis (2-sulfanylethyl)amine {NH(CH$_2$CH$_2$SH)$_2$—HCl}.

In a 1.5 mL Eppendorf tube, bis(2-sulfanylethyl)amine {HN(CH$_2$CH$_2$SH)$_2$—HCl, 10% (w/v), 31.3 mg} dissolved in a 0.2 M citrate buffer solution containing 6M guanidine hydrochloride was added to a peptide (H-LQNIHC-OH) 8 (1 equivalent, 0.50 mg) to cause a reaction. The reaction was performed at 50° C. The reaction was tracked for 72 hours, and checked by LC/MS (FIG. 26). A result of mass spectrometry of a target product 9: M/Z 743.5.

The invention claimed is:

1. A method for producing a peptide thioester, comprising the steps of:
   (1) providing a peptide having the following sequence:

[Formula 1]

R—K-CGC-OOOH   (1)

wherein R represents any amino acid sequence, X represents any amino acid, and CGC-COOH represents cysteine-glycine-cysteine-COOH;

(2) causing a transfer between an SH group of the C-terminal cysteine and a carbonyl group of the glycine in the CGC triplet to obtain an R-X-CG-thioester; and (3) causing, in the R-X-CG-thioester, a transfer between the SH group of the cysteine and a carbonyl group of X, and ring-closure condensation between an amino group of the cysteine and a carbonyl group of the thioester of the glycine to obtain a peptide thioester.

2. The production method according to claim 1,
wherein the peptide having the sequence of Formula 1 is obtained by chemical synthesis, or expression by an expression system.

3. The production method according to claim 1,
wherein a reaction in the step (2) is performed in the presence of at least one thiol selected from the group consisting of sodium 2-mercaptoethanesulfonate (MESNa), 2-aminoethanethiol, and bis(2-sulfanylethyl)amine.

4. The production method according to claim 1,
wherein a reaction in the step (3) is performed in the presence of at least one thiol selected from sodium 2-mercaptoethanesulfonate (MESNa), mercaptophenylacetic acid (MPAA), 2-mercaptopropionic acid, thiophenol, benzyl mercaptan, and ¾-mercapto-benzylsulfonate.

5. The production method according to claim 1, further comprising
(2-1) purifying the R-X-CG-thioester after the reaction of the step (2) and before the step (3).

6. The production method according to claim 1,
wherein the peptide having the sequence of Formula 1 is a glycosylated peptide.

7. A method for producing a peptide, comprising a step of condensing:
(A) a peptide thioester produced by the production method according to claim 1; and
(B) an amino thioacid or peptide thioacid,
to obtain a peptide,
wherein at least some of side chains of amino acids constituting (A) and (B) is unprotected.

8. The method for producing a peptide according to claim 7,
wherein all of the side chains of the amino acids constituting (A) and (B) are unprotected.

9. The method for producing a peptide according to claim 7,
wherein the production method is a method for producing a glycosylated peptide, and wherein the peptide thioester is a glycosylated peptide thioester and/or the amino thioacid or peptide thioacid is a glycosylated amino thioacid or glycosylated peptide thioacid.

10. The method for producing a peptide according to claim 9,
wherein the glycosylated amino thioacid is a thioacid of a glycosylated amino acid selected from the group consisting of Asn, Ser, Thr, Hyl, and Hyp.

11. The method for producing a peptide according to claim 9,
wherein a glycosylated amino acid in the glycosylated peptide thioacid is a glycosylated amino acid selected from the group consisting of Asn, Ser, Thr, Hyl and Hyp.

12. The method for producing a peptide according to claim 9,
wherein the glycosylated peptide thioacid is obtained by reacting a glycosylated amino thioacid with a peptide having, at an N-terminal, a cysteine having, in a side chain thereof, a modifying group capable of forming a disulfide bond to a thioic acid group (—SH) in the glycosylated amino thioacid to introduce the thioic acid group into a C-terminal of the peptide resulting from the reaction.

13. The method for producing a peptide according to claim 12,
wherein the modifying group is a modifying group selected from the group consisting of:

[Formula 2]

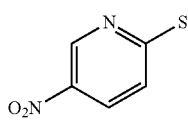

[Formula 3]

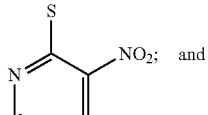

and

[Formula 4]

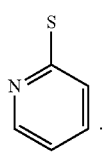

14. A method for producing a peptide, comprising a step of condensing:
(a) a peptide thioester produced by the production method according to claim 1; and
(b) an amino acid or peptide having an auxiliary group having the following structure introduced into an N-terminal thereof:

X—C(SH)—Y          [Formula 5]

wherein X represents any substituent that can be separated by a separation treatment selected from the group consisting of an acid treatment, a base treatment, a light irradiation treatment, or a reduction treatment, wherein the separation treatment is performed at any stage after formation of a sulfide bond to the peptide thioester and formation of an amide bond by the S—N acyl transfer subsequently caused; and Y represents a ketone or an aldehyde, to obtain a peptide,
wherein at least some of side chains of amino acids constituting (a) and (b) is unprotected.

15. The method for producing a peptide according to claim 14,
wherein X represents aryl.

16. The method for producing a peptide according to claim 14,
wherein all of the side chains of the amino acids constituting (a) and (b) are unprotected.

17. The method for producing a peptide according to claim 14,
wherein the production method is a method for producing a glycosylated peptide, and wherein the peptide thioester is a glycosylated peptide thioester and/or the amino acid or peptide having an auxiliary group introduced into an N-terminal thereof is a glycosylated amino acid or glycosylated peptide having the auxiliary group introduced into an N-terminal thereof.

18. The method for producing a peptide according to claim 17,
wherein the glycosylated amino acid having the auxiliary group introduced into an N-terminal thereof is selected from the group consisting of glycosylated Asn, glycosylated Ser, glycosylated Thr, glycosylate Hyl, and glycosylate Hyp having the auxiliary group introduced into an N-terminal thereof.

19. The method for producing a peptide according to claim 18, wherein the glycosylated amino acid having the auxiliary group introduced into an N-terminal thereof is a glycosylated amino acid having the following structure:

[Formula 6]

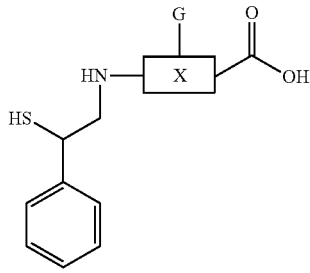

wherein X represents any amino acid, and G represents any sugar chain.

20. The method for producing a peptide according to claim 19, wherein the amino acid X is selected from the group consisting of Asn, Ser, Thr, and Hyl.

21. The method for producing a peptide according to claim 18, wherein the glycosylated amino acid having the auxiliary group introduced into an N-terminal thereof is a glycosylated dipeptide having the following structure:

[Formula 7]

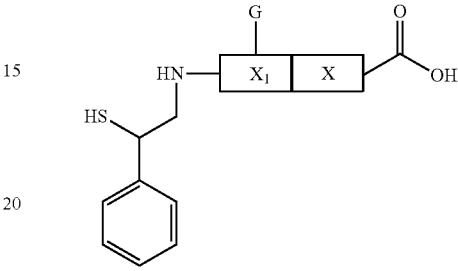

wherein $X_1$ represents Asn, Ser, Thr, or Hyl, X represents any amino acid, and G represents any sugar chain.

* * * * *

UNITED STATES PATENT AND TRADEMARK OFFICE
CERTIFICATE OF CORRECTION

PATENT NO. : 12,103,947 B2
APPLICATION NO. : 17/298125
DATED : October 1, 2024
INVENTOR(S) : Kajihara et al.

It is certified that error appears in the above-identified patent and that said Letters Patent is hereby corrected as shown below:

In the Specification

Column 2, Line 43: Please correct "RU-XT-TGC-COOH (C1)" to read --R-X-CGC-COOH (1)--

Column 18, Line 20: Please correct "a" to read --α--

Column 21, Line 35: Please delete formula 23 and replace with the following:

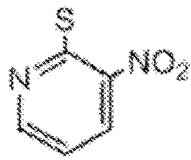

Column 24, Line 24: Please correct "$C_{19}$" to read --$C_{109}$--

Column 27, Line 1: Please correct "5.4 mol)" to read --5.4 μmol)--

Column 27, Line 16: Please correct "$[M+2H]^{2-}$" to read --$[M+2H]^{2+}$--

Column 30, Line 48: Please correct "(141 mol)" to read --(141 μmol)--

Column 33, Line 58: Please correct "$H_{178}$" to read --$H_{180}$--

Column 39, Line 8: Please correct "$C_{27}H_{24}02$" to read --$C_{27}H_{24}O_2$--

Column 39, Line 47: Please correct "$N_2H_4$—$H_2O$" to read --$N_2H_4 \cdot H_2O$--

Column 40, Line 42: Please correct "1H" to read --$^1H$--

Column 41, Line 3: Please correct "0-(tert-butyl)-L-serine" to read --O-(tert-butyl)-L-serine--

Signed and Sealed this
Seventeenth Day of December, 2024

Derrick Brent
*Acting Director of the United States Patent and Trademark Office*

CERTIFICATE OF CORRECTION (continued)
U.S. Pat. No. 12,103,947 B2

Column 43, Line 1: Please correct "Emoc-Asn" to read --Fmoc-Asn--

Column 45, Line 42: Please correct "3.68 mol)" to read --3.68 µmol)--

Column 51, Line 54: Please correct "17.9 mol," to read --17.9 µmol,--

Column 55, Line 27: Please correct "(GM" to read --(6M--

Column 58, Line 17: Please correct "{HN(CH$_2$CH$_2$SH)$_2$—HCl," to read --{HN(CH$_2$CH$_2$SH)$_2$·HCl,--

In the Claims

Column 58, Line 30, Claim 1: Please correct "R-K-CGC-OOOH" to read --R-X-CGC-COOH--